United States Patent
Setaluri et al.

(10) Patent No.: US 6,613,534 B2
(45) Date of Patent: Sep. 2, 2003

(54) MAP-2 AS A DETERMINANT OF METASTATIC POTENTIAL

(75) Inventors: Vijayasaradhi Setaluri, Winston-Salem, NC (US); Dong Fang, Winston-Salem, NC (US); Wain White, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 09/812,348

(22) Filed: Mar. 20, 2001

(65) Prior Publication Data

US 2002/0192727 A1 Dec. 19, 2002

(51) Int. Cl.$^7$ .............................................. G01N 33/574
(52) U.S. Cl. ........................ 435/7.23; 435/7.1; 435/975
(58) Field of Search ................................ 435/7.1, 7.23, 435/975

(56) References Cited

U.S. PATENT DOCUMENTS

| | | |
|---|---|---|
| 4,376,110 A | 3/1983 | David et al. |
| 4,394,448 A | 7/1983 | Szoka, Jr. et al. |
| 4,683,202 A | 7/1987 | Mullis |
| 4,843,155 A | 6/1989 | Chomczynski |
| 4,946,777 A | 8/1990 | Lameris et al. |
| 5,252,479 A | 10/1993 | Srivastava |
| 5,262,311 A | 11/1993 | Pardee et al. |
| 5,264,618 A | 11/1993 | Felgner et al. |
| 5,283,185 A | 2/1994 | Epand et al. |
| 5,334,761 A | 8/1994 | Gebeyehu et al. |
| 5,399,346 A | 3/1995 | Anderson et al. |
| 5,597,830 A | 1/1997 | Klohs et al. |
| 5,626,561 A | 5/1997 | Butler et al. |
| 5,633,161 A | 5/1997 | Shyjan |
| 5,656,465 A | 8/1997 | Panicali et al. |
| 5,674,739 A | 10/1997 | Shyjan |
| 5,714,353 A | 2/1998 | Pathak et al. |
| 5,719,131 A | 2/1998 | Harris et al. |
| 5,741,486 A | 4/1998 | Pathak et al. |
| 5,770,366 A | 6/1998 | Bogdahn et al. |
| 5,922,775 A | 7/1999 | Kun et al. |
| 6,025,137 A | 2/2000 | Shyjan |
| 6,057,105 A | 5/2000 | Hoon et al. |
| 6,080,727 A | 6/2000 | Zupi |
| 6,080,777 A | 6/2000 | Schiff |
| 6,083,703 A | 7/2000 | Wang et al. |
| 6,127,415 A | 10/2000 | Pfahl et al. |
| 6,135,976 A | 10/2000 | Tachibana et al. |
| 6,150,398 A | 11/2000 | Vande Woude et al. |
| 6,153,388 A | 11/2000 | Reintgen |
| 6,156,564 A | 12/2000 | Pastan et al. |
| 6,162,930 A | 12/2000 | Pinney et al. |
| 6,168,916 B1 | 1/2001 | Kingsman et al. |
| 6,168,946 B1 | 1/2001 | Houghton et al. |
| 6,191,290 B1 | 2/2001 | Safavy |

FOREIGN PATENT DOCUMENTS

| | | |
|---|---|---|
| WO | 34336 | *6/2000 |

OTHER PUBLICATIONS

Kobori, Koyoto–furitsu Ika Daigaku Zasshi, 130(3) 371 !994.*
Veita et al, Br. J. Cancer. vol. 78 p. 871 1998.*
Aouani, A. et al., *Hexamethylene Bisacetamide (HMBA) Increases Thyroglobulin Levels in Porcine Thyroid Cells Without Increasing Cyclic–AMP*, Metab. Res. 31:402–5 (1999).
Ausubel, F.M. et al., *Short Protocols in Molecular Biology* (4$^{th}$ Ed.), Title Pages (front & back), Table of Contents, pp. 1–27–1–29, Chapter 2, 4–1–4–12, Chapter 9, Chapter 16, & index, John Wiley and Sons, Inc. 1999.
Bird, R. et al., *Single–Chain Antigen–Binding Proteins*, Science 242:423–6 (1988).
Bitter, G. et al., *Expression and Secretion Vectors for Yeast*, Methods in Enzyol. 153:516–44 (1987).
Boring et al., *Cancer Statistics, 1993*, CA Cancer J Clin 1993:43:7–26.
Carey, T.E. et al., *Cell Surface antigens of human malignant melanoma: Mixed hemadsorption assays for humoral immunity to cultured autologous melanoma cells*, Proc. Natl. Acad. Sci. USA 73:3278–82 (1976).
Dhillon, A. et al., *Neurone specific enolase: an aid to the diagnosis of melanoma and neuroblastoma*, Histopathology 6:81–92 (1982).
Elder, D. et al., *Antigenic Profile of Tumor Progression Stages in Human Melanocytic Nevi and Melanomas*, Cancer Research 49:5091–96 (1989).
Encinas, M. et al., *Sequential Treatment of SH–SY5Y Cells with Retinoic Acid and Brain–Derived Neurotrophic Factor Gives Rise to Fully Differentiated, Neurotrophic Factor–Dependent, Human Neuron–Like Cells*, J. Neurochem. 75:991–1003 (2000).
Fang, D. et al., *Role of Microphthalmia Transcription Factor in Regulation of Melanocyte Differentiation Marker TRP–1*, Biochem Biophys. Res. Commun. 256:657–63 (1999).
Garner, C. et al., *Different Forms of Microtubule–associated Protein 2 Are Encoded by Separate mRNA Transcripts*, J. Cell Biol. 106:779–83 (1988).

(List continued on next page.)

Primary Examiner—Sheela Huff
(74) Attorney, Agent, or Firm—Cynthia B. Rothschild; Charles W. Calkins; Kilpatrick Stockton LLP

(57) ABSTRACT

The invention relates to detection of MAP-2 (microtubule associated protein-2) as a marker to determine the metastatic potential of a tumor, including tumors derived from the neural crest such as melanomas, gliomas, Schwanomas, chromocytomas and small cell lung cancer. In one aspect, the invention comprises a method for determining the metastatic potential of a tumor sample, wherein decreased levels of MAP-2 expression in a test sample relative to controls indicates that the sample has increased metastatic potential as compared to the control. In another aspect, the invention comprises a method to prevent tumor progression in metastatic melanoma by increasing levels of MAP-2 protein in cells.

19 Claims, 8 Drawing Sheets

(1 of 8 Drawing Sheet(s) Filed in Color)

OTHER PUBLICATIONS

Gen Bank Accession No. XM 002387 available at http://www.ncbi.nlm.nih.gov/entrez.

Gen Bank Accession No. U32996 available at http:..www.ncbi.nlm.nih.gov/entrez.

Gen Bank Accession No. NM002374 available at http://www.ncbi.nlm.nih.gov/entrez.

Houghton, A. et al., *Phenotypic Heterogeneity of Melanoma*, J. Exp. Med. 164: 812–29 (1987).

Khare, V. et al., *The neuropeptide/mast cell secretagogue substance P is expressed in cutaneous melanocytic lesions*, J. Cutan Pathol. 25:2–10 (1998).

Kobayash, N. et al., *A role of microtubules during the formation of cell processes in neuronal and non–neuronal cells*, Cell Tissue Res. 291:163–174 (1998).

Lammerding–Koppel, M. et al., *Immunohistochemical localization of muscarinic acetylcholine receptors in primary and metastatic melanomas*, J. Cutan. Pathol. 25:137–144 (1997).

Le Douarin, N., *The Neural Crest*, Cambridge University Press 1982.

Leclerc, N. et al., *Juvenile and Mature MAP2 Isoforms Induce Distinct Patterns of Process Outgrowth*, Mol. Biol. Cell 7:443–455 (1996).

Leng, L. et al., *Differential Modulation of Protein Kinase C Isoforms in Erythroleukemia during Induced Differentiation*, Cancer Res. 53:5554–5558 (1993).

Lim, R. et al., *Regulated Association of Microtubule–associated Protein 2 (MAP2) with Src and Grb2: Evidence for MAP2 as a Scaffolding Protein*, J. Biol. Chem. 275:20578–20587 (2000).

Logan, J. et al., *Adenovirus tripartite leader sequence enhances translation of mRNA late after infection*, Proc. Natl. Acad. Sci. USA 81:3655–3659 (1984).

Maniatis, *Molecular Cloning* ($2^{nd}$ Ed.), Title Cover, Table of Contents, Index, Chapter 16 and 17, Cold Spring Harbor Laboratory (1989).

Matus, A., *Microtubule–Associated Proteins: The Potential Role in Determining Neuronal Morphology*, Ann. Rev. Neurosci. 11:29–44 (1988).

Needleman, S. et al., *A General Method Applicable to the Search for Similarities in the Amino Acid Sequence of Two Proteins*, J. Mol. Biol. 48:443–453 (1970).

Pearson, W. et al., *Improved tools for biological sequence comparison*, Proc. Natl. Acad. Sci. USA 85:2444–48 (1988).

Prieto, V. et al., *The intermediate filament peripherin is expressed in cutaneous melanocytic lesions*, J. Cutan. Pathol. 24:145–150 (1997).

Reed, J. et al., *Divergent Cellular Differentiation Pathways during the Invasive Stage of Cutaneous Malignant Melanoma Progression*, Am. J. Pathol. 155:549–555 (1999).

Richon, V. et al., *A class of hybrid polar inducers of transformed cell differentiation inhibits histone deacetylases*, Proc. Natl. Acad. Sci. USA 95:3003–07 (1998).

Rifkind, R. et al., *Induced Differentiation, the Cell Cycle, and the Treatment of Cancer*, Pharmacol. Ther. 69:97–102 (1996).

Robbins, Perry & Perez, Marita, *Understanding Melonoma; What You Need to Know*, Complete Pamphlet, The Skin Cancer Foundation (1996).

Rodeck, U. et al., *Metastatic But Not Primary Melanoma Cell Lines Grow In Vitro Independently of Exogenous Growth Factors*, Int. J. Cancer 40:687–90 (1987).

Roy, N. et al., *In vitro neurogenesis by progenitor cells isolated from the adult human hippocampus*, Nat. Med. 6:271–277 (2000).

Sangueza, O. et al., *Neoplasmas with Neural Differentiation: A Review*, Am. J. Dermatopath. 20:89–102 (1988).

Satyamoorthy, K. et al., *Melanoma cell lines from different stages of progression and their biological and molecular analyses*, Melanoma Res. 7:S35–42 (1997).

Scheele, J., *camp–dependent phosphorylation and hexamethylene–bis–acetamide induced dephosphorylation of p19 in murine erythroleukemia cells*, Mol. Cell. Biochem. 185:55–63 (1998).

Smith, Temple F. & Waterman, Michael S., *Comparison of Biosequences*, Advances in Applied Mathematics 2, 482–489 (1981).

Tojima, T. et al., *Acquistion of neuronal proteins during differentiation of NG108–15 cells*, Neurosci. Res. 37:153–161 (2000).

Vijayasaradhi, S. et al., *Melanocyte Differentiation Marker gp75, the Brown Locus Protein, Can Be Regulated Independently of Tyrosinase and Pigmentation*, J. Invest. Dermatol. 105:113–19 (1995).

\* cited by examiner

A.
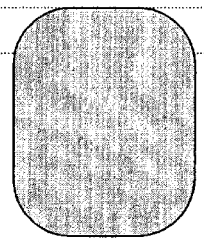
Primary Invasive Melanoma
B.
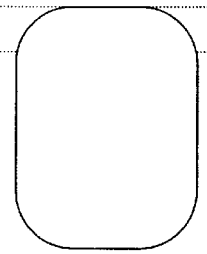
Metastatic Melanoma
Figure 1

SEQ ID NO: 1 (5' to 3') MAP-2 DNA Probe    A

GGATCTGAGCCATTAAAATCAAATGGTCCACTAGGCGTATGATCTCTTTGAGC

CAAATCAGTTCCTGAATATAAAGGAGGAAATGATGAGGATGTACTGAGGCTA

ACGGGGCAAGTATAGAAACATCCAAGACAAAAGCCTAAGGGATGCAAAGGC

AGAGACACAGGTGCTTTTGGTGACCCAGTGGATATGGCAACCAGTGTAACT

GCCATACAAGAAACCCTAGGAGCAAACCCACACCACTCATTCTCAGCTAAGA

GATTTTACACAGGCAAACGTGTCTTAAACCATCTATAAATCAGTTATTTTATA

TGACAGTCAAAACCTTAGAAACCTTAGGATCATTATATCTATTTTCTGCCTAT

TAATTGCTGTGAGGTTTGATTTGACCAATCTGGGCAATTTATTCATCAGCTTC

C CTTGAAGTGCACCAGAAAATAGAAGAAGGTGTG

SEQ ID NO: 2 (5' to 3')  MAP2c-F Primer    B

ATCAAATGGTCCACTAGGCG

SEQ ID NO: 3 (5' to 3') MAP2c-R Primer    C

GCACTTCAAGGGAAGCTGAT

Figure 2

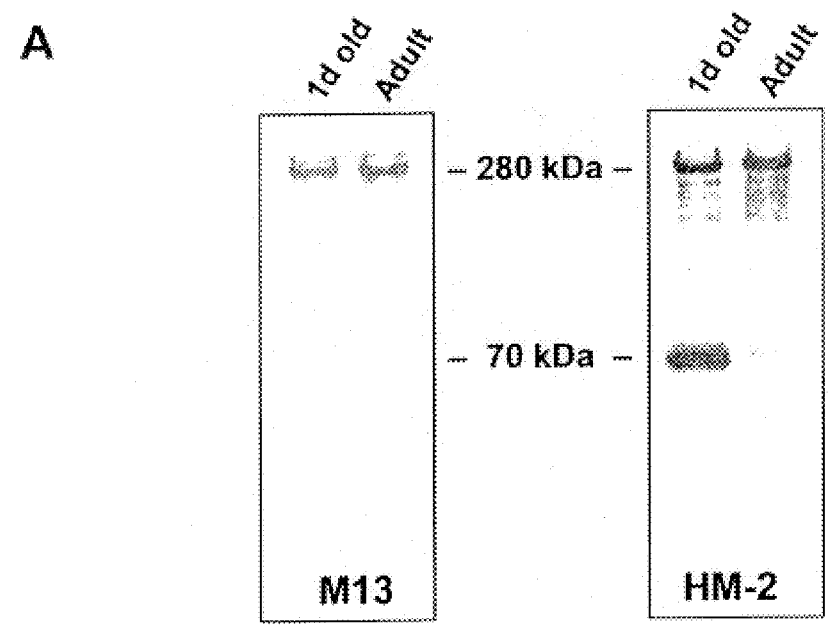
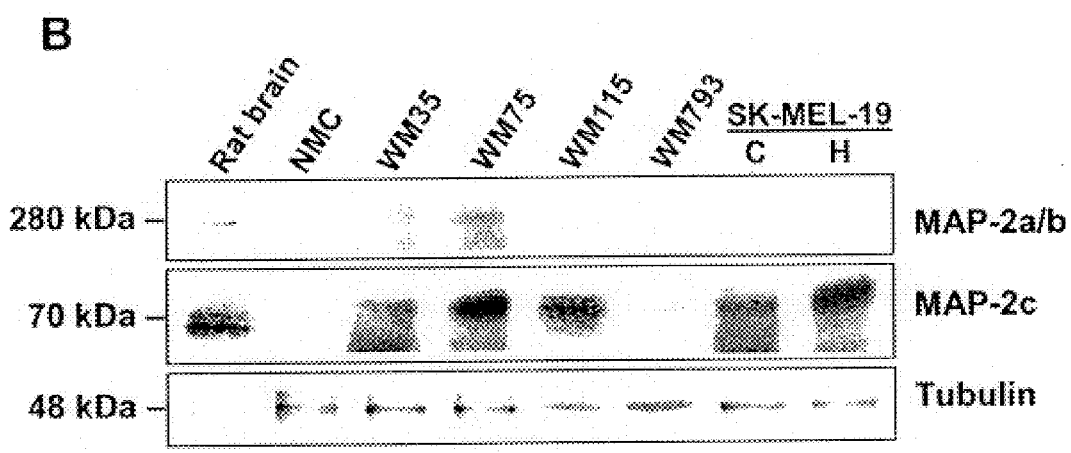
Figure 6

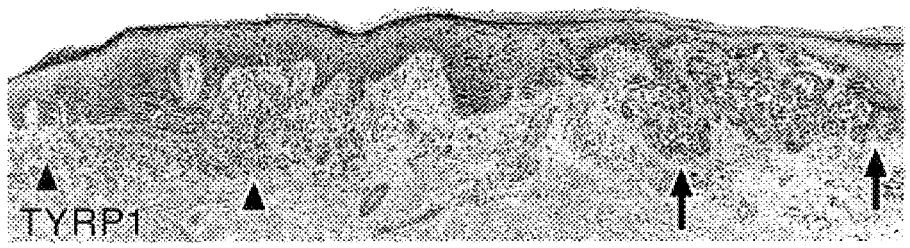
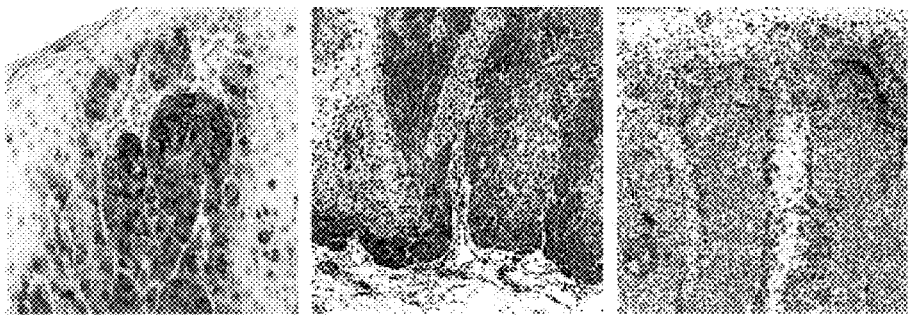
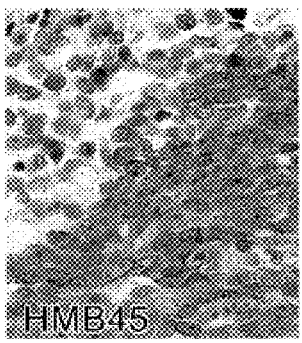
FIG. 7

SEQUENCE LISTING

```
<160> NUMBER OF SEQ ID NOS: 7

<210> SEQ ID NO 1
<211> LENGTH: 454
<212> TYPE: DNA
<213> ORGANISM: Homo sapiens

<400> SEQUENCE: 1
ggatctgagc cattaaaatc aaatggtcca ctaggcgtat gatctctttg agccaaatca      60
gttcctgaat ataaggagg aaatgatgag gatgtactga ggctaacggg gcaagtatag      120
aaacatccaa gacaaaagcc taagggatgc aaaggcagag acacaggtgc tttttggtga     180
cccagtggat atggcaacca gtgtaactgc catacaagaa accctaggag caaacccaca     240
ccactcattc tcagctaaga gattttacac aggcaaacgt gtcttaaacc atctataaat     300
cagttatttt atatgacagt caaaaccta gaaaccttag gatcattata tctattttct      360
gcctattaat tgctgtgagg tttgatttga ccaatctggg caatttattc atcagcttcc     420
cttgaagtgc accagaaaat agaagaaagg tgtg                                 454

<210> SEQ ID NO 2
<211> LENGTH: 20
<212> TYPE: DNA
<213> ORGANISM: Artificial Sequence
<220> FEATURE:
<223> OTHER INFORMATION: MAP2c-F Primer
```

-continued

```
<400> SEQUENCE: 2
atcaaatggt ccactaggcg                                              20

<210> SEQ ID NO 3
<211> LENGTH: 20
<212> TYPE: DNA
<213> ORGANISM: Artificial Sequence
<220> FEATURE:
<223> OTHER INFORMATION: MAP2c-R Primer

<400> SEQUENCE: 3
gcacttcaag ggaagctgat                                              20

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 4
attaaccctc actaaatgct ggtag                                        25

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 5
cattatgctg agtgatatct ttttttttga                                   30

<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 6
atctggcacc acaccttcta caatgagctg cg                                32

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 7
cgtcatactc ctgcttgctg atccacatct gc                                32
```

MAP-2 AS A DETERMINANT OF METASTATIC POTENTIAL

STATEMENT REGARDING FEDERALLY SPONSORED RESEARCH AND DEVELOPMENT

Portions of this work were funded by the National Institutes of Health (NIH) grants AR44617 and NS30985 and a Dermik Laboratory Research Fellowship grant from the Dermatology Foundation.

FIELD OF THE INVENTION

The invention relates to methods for the detection, diagnosis, prognosis and treatment of cancer. Specifically, the invention describes the detection of microtubule associated protein—2 (MAP-2) in tumor cells, and the use of MAP-2 as an indicator of metastatic potential. The invention also describes the use of MAP-2 to prevent non-metastatic primary tumors from progressing to later stage disease.

BACKGROUND OF THE INVENTION

Publications referred to throughout the text of this document are incorporated by reference in their entireties in order to more fully describe the state of the art as known to those skilled therein as of the date of the invention described and claimed herein.

Cancer is the second leading cause of death in the United States after heart disease (Boring et al., *CA Cancer J. Clin.*, 43:7 (1993)). Cancer is characterized by the growth of abnormal (neoplastic) cells which develop from normal tissue. In cancer, cells acquire the ability to override normal constraints on the cell and proliferate under conditions in which normal cells would not grow. Among the most potent cancer causing agents (carcinogens) are ultraviolet and ionizing forms of radiation. Thus, cancer is a typically a disease of malfunctioning cellular genes (or unwanted viral expression) which leads to unchecked growth of tissue. It is generally accepted that multiple mutations must occur to cause cancer, and that cells must progress through several steps in the transformation from normal cells to an early-stage tumor and finally, to invasive and metastatic disease.

Cancer arises from a deregulation in the communication between tumor cells and their environment. Normally, cells do not divide in the absence of stimulatory signals. In cancer, this control is lost, and the cell is able to override its normal quiescent state and proliferate without restriction. Once a tumor reaches a certain size, however, growth is limited by diffusion of nutrients through the tumor. At this point tumors may generate angiogenic factors which promote neovascularization of the tumor and allow for tumor cells to be carried to distant sites in a process known as metastasis. A variety of factors have been implicated in metastasis including growth factors, cell surface receptors, and cytokines which modulate cell division.

For example, melanoma is a type of skin cancer which, if not removed while confined to the upper layers of the skin, spreads internally and is usually fatal. There are four stages of melanoma. Stages I and II are early stages of the disease, and are classified according to the thickness of the tumor, known as the Breslow's thickness, and by the number of layers of skin invaded by the tumor, known as the Clark's level of invasion (see e.g. Robbins, P. and Perez, M., *Understanding Melanoma: What You Need to Know*, The Skin Cancer Foundation (1996)). Stages III and IV, the more advanced stages of the disease, are classified according to the degree of melanoma spread beyond the skin. By Stage III, the tumor has metastasized to lymph nodes in the region of the original tumor or nearby skin. At this point, Breslow thickness and Clark's level are no longer described in the diagnosis. Finally, by Stage IV, the melanoma has metastasized to lymph nodes far away from the primary tumor or to internal organs, such as the lung, liver, brain, bone and gastrointestinal tract. Later stages of cancer generally require that alternative diagnostic and preventative tools be invoked. For example, Stage III melanoma may require evaluation of the lymph nodes. With distant metastases (i.e. Stage IV), the physician may call for imaging of the head, chest, abdomen and pelvis. Finally, chemotherapy and immunotherapy treatments may be invoked.

Methods for the general detection of genes for cancer diagnosis and prevention of tumor progression are described in U.S. Pat. Nos. 6,025,137, 5,674,739 and 5,633,161, which describe methods for detection of genes differentially expressed in cancer and the identification of mouse and human fomy030 gene in melanoma cells. For example, with respect to melanoma, markers include tyrosinase (U.S. Pat. No. 6,153,388), and tyrosinase, MART-1, and MAGE-3 (U.S. Pat. No. 6,057,105). Additionally, the use of gp75 antigen (TRP-1) as a tumor vaccine for melanoma is described in U.S. Pat. No. 6,168,946, and the use of TRP-2 protein as a tumor antigen is described in U.S. Pat. No. 6,083,703.

In light of the increasing importance of cancer, there is a need to identify methods which will improve cancer detection and diagnostics. Also, there is a need for markers which may be used by a physician to establish a prognosis which includes an evaluation of the risk of metastatic disease. Such diagnostic markers may be highly significant in cancers such as melanoma, where tumors may be detected early. Also, there is a need to develop compounds which can prevent or reduce the transformation of primary (benign) tumors into metastatic disease.

SUMMARY OF THE INVENTION

The invention describes detection of microtubule associated protein—2 (MAP-2) protein in tumor cells and the use of MAP-2 as a marker to assess the metastatic potential of tumor cells. Specifically, the invention describes that a decrease in MAP-2 expression in tumors is associated with metastatic disease. In one aspect, the invention comprises a method for detecting MAP-2 protein in a sample comprising tumor cells comprising the steps of: obtaining a test sample comprising tumor cells; incubating the cells with a detection agent that forms a complex with MAP-2 protein or fragments thereof; and detecting the presence of MAP-2 protein. The cellular membrane of the cells may be disrupted to allow access to intracellular proteins. In embodiments of the present invention, the presence of MAP-2 protein may be detected by detecting the presence of a complex formed between the detection agent and the MAP-2 protein.

It may be preferable to measure MAP-2 expression as levels of MAP-2 mRNA or cDNA in tumor cells. Thus, in another aspect, the invention comprises a method for detecting MAP-2 mRNA in a sample comprising tumor cells comprising the steps of: obtaining a sample comprising tumor cells; exposing the sample under high stringency conditions to at least one isolated nucleic acid that hybridizes to MAP-2 mRNA; and determining the levels MAP-2 mRNA based on the hybridization of the nucleic acid to MAP-2 mRNA.

In another aspect, the invention comprises a method for determining the metastatic potential of a tumor sample comprising the steps of: obtaining a test tumor sample of unknown metastatic potential from a subject; determining the level of MAP-2 expression in the test sample; and assessing the metastatic potential of the sample based on the level of MAP-2 expression in the test sample relative to a non-metastatic control comprising cells of the same or a similar tumor type.

Because an increase MAP-2 expression is associated with reduced metastatic potential, the invention contemplates that modulators of MAP-2 expression comprise potential anti-tumor agents. Thus, in another aspect, the invention comprises a method for screening for compounds that modulate MAP-2 expression comprising: incubating cells with a compound of interest; disrupting the cellular membrane of the cells to allow access to intracellular proteins; incubating the cell proteins with a detection agent which recognizes and complexes with MAP-2 protein or fragments thereof; detecting the presence of the complex; and comparing the levels of MAP-2 protein in cells treated with the compound of interest to the levels of MAP-2 protein in cells not incubated with the compound of interest.

Alternatively, the method of screening may measure MAP-2 mRNA or cDNA levels as a means of screening for compounds that modulate MAP-2 expression. Thus, in another aspect, the invention comprises a method for screening for compounds that modulate MAP-2 expression comprising: incubating cells with a compound of interest; exposing the cells under high stringency conditions to at least one isolated nucleic acid that hybridizes to MAP-2 mRNA; and determining the levels of MAP-2 mRNA based on the hybridization of the nucleic acid to MAP-2 mRNA; and comparing the levels of MAP-2 mRNA in cells treated with the compound of interest as compared to cells not incubated with the compound of interest.

In that expression of MAP-2 is strongest in primary tumors, with a decrease as cells progress to later stages of cancer, MAP-2 may be used to prevent early stage tumors from progressing to later stage diseases. Thus, in another aspect, the invention comprises a method to prevent tumor progression in metastatic melanoma comprising increasing levels of MAP-2 expression in cells.

In yet another aspect, the invention includes the development of kits comprising reagents for performing the methods of the invention.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the components set forth in the following description and drawings. The invention is capable of other embodiments and of being practiced or carried out in various ways.

From the foregoing summary, it is apparent that an object of the present invention is to provide a method for the use of MAP-2 as a marker to assess the metastatic potential of tumors such as melanoma and other tumors of neural crest derived tissue. The invention also describes the use of MAP-2 to prevent tumor progression by increasing levels of MAP-2 protein in cells. These, together with other objects of the present invention, along with the various features of novelty which characterize the invention, are pointed out with particularity in the claims annexed to and forming a part of this document.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

Various features, aspects and advantages of the present invention will become more apparent with reference to the following description, appended claims, and accompanying drawings.

FIG. 1 shows an aspect of an embodiment of the invention comprising a schematic of the up-regulation of MAP-2 in primary invasive melanoma (panel A) and the reduced expression of MAP-2 in metastatic disease (Panel B).

FIG. 2 shows an aspect of an embodiment of the invention comprising: (A) SEQ ID NO: 1, the nucleotide sequence for a 450 bp fragment of MAP-2 mRNA; (B) SEQ ID NO: 2, the nucleotide sequence for primer MAP-2cF used for RT-PCR amplification of MAP-2 mRNA sequences; and (C) SEQ ID NO: 3, the nucleotide sequence for primer MAP-2cR used for RT-PCR amplification of MAP-2 mRNA sequences.

FIG. 6 shows an aspect of an embodiment of the invention comprising immunoblotting analysis of MAP-2 expression in melanocytes and melanoma wherein (A) shows the specificity of anti-MAP-2 mAbs M13 and HM-2, and (B) shows extracts of melanocytes and melanoma cells analyzed by western blotting using mAb HM-2 using the following cell lines: Rat brain—1 day old rat brain extract positive control; NMC—melanocytes; WM35—a RGP primary melanoma cell line, WM75, WM115, WM793 —VGP primary melanoma cell lines; C—control SK-MEL-19 cells; and H—5 day HMBA treated SK-MEL-19 cells, where immunoblotting with polyclonal anti-γ-tubulin is shown to estimate variation in amount of protein loaded in each lane.

FIG. 7 shows an aspect of an embodiment of the invention comprising immunohistochemical analysis of MAP-2 expression in melanocytic lesions wherein (A) shows primary malignant melanoma (superficial spreading type, Breslow thickness 0.5 mm, Clark level III) arising in association with a melanocytic nevus stained with MAP-2 (upper panels) and TYRP1 (lower panels) wherein the middle and right panels show higher magnification of the areas marked with asterisks, arrowheads demarcate the approximate boundaries of the melanocytic nevus, and the arrows indicate the melanoma; and (B) shows the reciprocal expression of TYRP1 and MAP-2 in a primary malignant melanoma (Breslow thickness 1.14 mm, Clark level III) with in situ and invasive components wherein staining of invasive melanoma cells by anti-MAP-2 mAb is indicated by arrows, staining for TYRP1 at the junction of in situ and dermal components of the tumor highlighted by arrowheads, and staining for gp100 (HMB45) confirms melanocyte differentiation; and (C) shows the reciprocal expression of TYRP1 and MAP-2 in a metastatic melanoma wherein HMB45 staining is used to confirm melanocytic differentiation of the metastatic lesion.

DETAILED DESCRIPTION OF THE INVENTION

Figure 3:
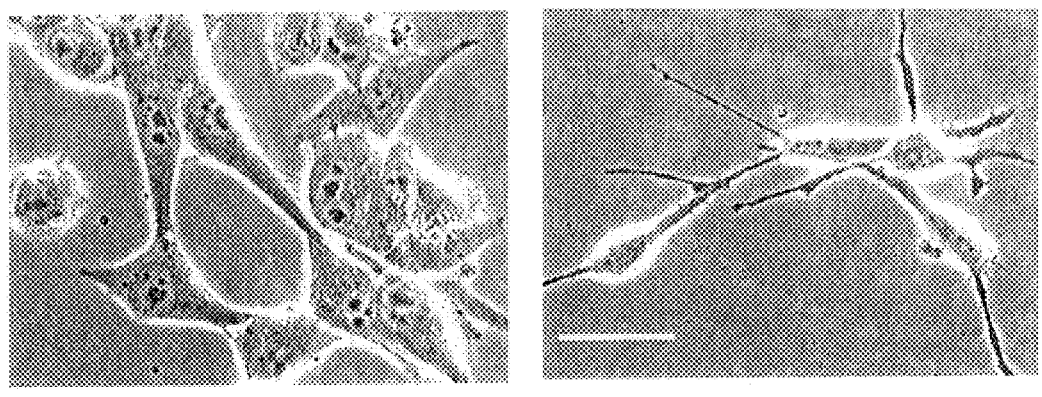
FIG. 3 shows induction of dendritic morphology in the human metastatic melanoma cell line SK-MEL-19 treated with 5 mM hexamethylene bisacetamide (HMBA) for 5 days (bar: 100 μm).

The invention describes detection of microtubule associated protein—2 (MAP-2) protein in tumor cells and the use of MAP-2 as a marker to assess the metastatic potential of tumor cells. In one aspect, the invention comprises a method for detecting MAP-2 protein in a sample comprising tumor cells comprising the steps of: obtaining a test sample comprising tumor cells; incubating the cells with a detection agent that forms a complex with MAP-2 protein or fragments thereof; and detecting the presence of the MAP-2 protein. The method may further comprise disrupting the cellular membrane of the cells to allow access to intracellular proteins. In an embodiment, the detection agent comprises antibody that recognizes MAP-2 protein or a fragment thereof.

Preferably, the tumor cells comprise tissue derived from the neural crest. More preferably, the tumor cells comprise melanoma cells.

The levels of MAP-2 protein may be compared to known exogenous standards, or to controls from tumors of the same or a similar tumor type. In an embodiment, the method includes comparing the levels of MAP-2 protein in the sample relative to at least one control comprising known amounts of MAP-2. Preferably, the method also includes the step of assessing the risk of whether the tumor sample comprises increased metastatic potential based on the level of MAP-2 in the tumor relative to the control.

In another embodiment, the method includes the steps of: obtaining a control sample comprising non-metastatic cells of the same or a similar tumor type; determining whether MAP-2 protein or fragments thereof are present in the control sample; and comparing the amount of MAP-2 in the test sample relative to the control sample. Preferably, the presence of decreased levels of MAP-2 protein in the test sample relative to the level of MAP-2 in non-metastatic control cells from the same or a similar tumor type indicates that the test sample has increased metastatic potential as compared to the control. More preferably, the test sample comprises invasive melanoma.

Preferably, the test sample is from a patient. More preferably, reduced MAP-2 mRNA in the test sample as compared to a non-metastatic control indicates the test subject is at risk of developing metastatic disease.

It may be preferable to measure MAP-2 expression as levels of MAP-2 mRNA or cDNA in tumor cells. Thus, in another aspect, the invention comprises a method for detecting MAP-2 mRNA in a sample comprising tumor cells having the steps of: obtaining a sample comprising tumor cells; exposing the sample under high stringency conditions to at least one isolated nucleic acid that hybridizes to MAP-2 mRNA; and determining the levels of MAP-2 mRNA based on the hybridization of the nucleic acid to MAP-2 mRNA. In an embodiment, the isolated nucleic acid that hybridizes to MAP-2 mRNA comprises the nucleic acid sequence complementary to SEQ ID NO: 1 or a fragment thereof. Preferably, the method farther includes the steps of preparing MAP-2 cDNA using mRNA isolated from the test sample as a template; conducting polymerase chain reaction (PCR) amplification using primers specific for the MAP-2 gene comprising amplification conditions such that a PCR product is generated in cells comprising MAP-2 mRNA but not in cells which do not comprise MAP-2 mRNA; and detecting the MAP-2 specific PCR product. In an embodiment, the primers specific for the MAP-2 gene comprise oligonucleotides comprising the nucleic acid sequence SEQ ID NO: 2 and SEQ ID NO: 3.

Preferably, the tumor cells comprise tissue derived from the neural crest. More preferably, the tumor cells comprise melanoma cells.

The levels of MAP-2 mRNA may be compared to known exogenous standards, or to controls from tumors of the same or a similar tumor type. In an embodiment, the method incudes comparing the levels of MAP-2 protein in the sample relative to at least one control comprising known amounts of MAP-2. Preferably, the method also includes assessing the risk of whether the tumor sample comprises increased metastatic potential based on the level of MAP-2 mRNA in the test sample relative to the control.

In an embodiment, the method further comprises obtaining a control sample comprising a non-metastatic tumor cells from the same or a similar tumor type as the test sample; determining whether MAP-2 mRNA is present in the control sample; and determining the amount of MAP-2 mRNA in the test sample relative to the control sample. Preferably, the presence of decreased levels of MAP-2 mRNA in the test sample relative to the level of mRNA in control cells from the same or a similar tumor type indicates that the test sample has increased metastatic potential as compared to the control. Preferably, the test sample comprises invasive melanoma. Also preferably, the test sample is from a test subject. Even more preferably, reduced MAP-2 mRNA in the test sample as compared to a non-metastatic control indicates that the test subject is at risk of developing metastatic disease.

The invention comprises the discovery that MAP-2 expression in tumor cells is inversely related to metastatic potential. In another aspect, the invention comprises a method for determining the metastatic potential of a tumor sample comprising the steps of: obtaining a test tumor sample of unknown metastatic potential from a subject; determining the level of MAP-2 expression in the test sample; and assessing the metastatic potential of the sample based on the level of MAP-2 expression in the test sample relative to a non-metastatic control comprising cells of the same or a similar tumor type. Preferably,the presence of decreased levels of MAP-2 expression in the test sample relative to the level of MAP-2 expression in non-metastatic controls of the same or a similar tumor type indicates that the sample has increased metastatic potential as compared to the control. Also preferably, the levels of MAP-2 expression is assessed in comparison to controls comprising known amounts of MAP-2.

In an embodiment, the level of MAP-2 expression in cells from the sample and the control is assessed by measuring the level of MAP-2 protein, or fragments thereof, in said cells. Preferably, measuring the level of MAP-2 protein comprises the steps of disrupting the cellular membrane of the cells to allow access to intracellular proteins; incubating the cell proteins with a detection agent which recognizes and complexes with MAP-2 protein or fragments thereof; and detecting the presence of the complex. Preferably, the detection agent comprises antibody which recognizes MAP-2 protein or a fragment thereof.

In an embodiment, the level of MAP-2 expression in cells from the sample and the control is assessed by detection of MAP-2 mRNA or sequences substantially homologous thereto in the cells. Preferably, the detection of MAP-2 mRNA includes the steps of exposing the sample cells and the control cells under high stringency conditions to at least one isolated nucleic acid that hybridizes to MAP-2 mRNA; and detecting MAP-2 mRNA in the cells as the hybridization of the nucleic acid to MAP-2 mRNA. In an embodiment, the isolated nucleic acid that hybridizes to MAP-2 mRNA comprises the nucleic acid sequence complementary to SEQ ID NO: 1 or a fragment thereof More preferably, the detection of MAP-2 mRNA includes the steps of: preparing MAP-2 cDNA using mRNA isolated from the sample cells and the control cells as a template; conducting polymerase chain reaction (PCR) amplification using primers specific for the MAP-2 gene with amplification conditions such that a PCR product is generated in cells comprising MAP-2 mRNA but not in cells which do not comprise MAP-2 mRNA; and detecting the MAP-2 specific PCR product. Even more preferably, the primers specific for the MAP-2 gene comprise oligonucleotides comprising the nucleic acid sequence SEQ ID NO: 2 and SEQ ID NO: 3.

Preferably, the sample comprises tumor cells. More preferably, the sample comprises tumor cells derived from the neural crest. Even more preferably, the sample comprises melanoma cells. Even more preferably, the sample comprises invasive melanoma.

Preferably, the test sample is from a patient. More preferably, reduced MAP-2 expression in the test sample as compared to a non-metastatic control indicates the test subject is at risk of developing metastatic disease.

Because increase MAP-2 is associated with reduced metastatic potential, the invention contemplates that modulators of MAP-2 expression comprise potential anti-tumor agents. Thus, in another aspect, the invention comprises a method for screening for compounds that modulate MAP-2 expression comprising: incubating cells with a compound of interest; disrupting the cellular membrane of the cells to allow access to intracellular proteins; incubating the cell proteins with a detection agent which recognizes and complexes with MAP-2 protein or fragments thereof; detecting the presence of the complex; and comparing the levels of MAP-2 protein in cells treated with the compound of interest to the levels of MAP-2 protein in cells not incubated with the compound of interest.

Preferably, the detection agent comprises antibody which recognizes MAP-2 protein or a fragment thereof. Also preferably, the tumor cells comprise tissue derived from the neural crest. More preferably, the tumor cells comprise melanoma cells. Even more preferably, the tumor cells comprise metastatic melanoma cells. In an embodiment, the assay comprises multiple aliquots of tumor cell samples in an array.

Alternatively, the method of screening may measure MAP-2 mRNA or cDNA levels as a means of screening for compounds that modulate MAP-2 expression. Thus, in another aspect, the invention comprises a method for screening for compounds that modulate MAP-2 expression comprising incubating cells with a compound of interest; exposing the cells under high stringency conditions to at least one isolated nucleic acid that hybridizes to MAP-2 mRNA; determining the levels MAP-2 mRNA based on the hybridization of the nucleic acid with MAP-2 mRNA; and comparing the levels of MAP-2 mRNA in cells treated with the compound of interest as compared to cells not incubated with the compound of interest. In an embodiment, the isolated nucleic acid that hybridizes to MAP-2 mRNA comprises the nucleic acid sequence complementary to SEQ ID NO: 1 or a fragment thereof. Preferably, the assay further comprises the steps of preparing MAP-2 cDNA using cellular mRNA from the cells as a template; conducting polymerase chain reaction (PCR) amplification using primers specific for the MAP-2 gene with amplification conditions such that a PCR product is generated in cells comprising MAP-2 mRNA but not in cells which do not comprise MAP-2 mRNA; and detecting the MAP-2 specific PCR product. Even more preferably, the primers specific for the MAP-2 gene comprise oligonucleotides comprising the nucleic acid sequence SEQ ID NO: 2 and SEQ ID NO: 3. Also preferably, the tumor cells comprise tissue derived from the neural crest. More preferably, the tumor cells comprise melanoma cells. Even more preferably, the tumor cells comprise metastatic melanoma cells. In an embodiment, the assay comprises multiple aliquots of tumor cell samples in an array.

In that expression of MAP-2 is strongest in primary tumors, with a decrease as cells progress to later stages of cancer, MAP-2 may be used to prevent early stage tumors from progressing to later stage diseases. Thus, in another aspect, the invention comprises a method to prevent tumor progression comprising increasing levels of MAP-2 expression in cells. In an embodiment the method comprises increasing MAP-2 protein levels. In an embodiment, the method comprises increasing MAP-2 mRNA levels. In an embodiment, the increase in levels of MAP-2 is induced by exogenous compounds. Preferably, the exogenous compounds comprise differentiation inducing agents such as hexamethylene bisacetamide (HMBA), suberoylanilide hydroxamic acid (SAHA), and m-carboxycinnamic acid bishydroxamide (CBHA). More preferably, the treatment includes administration of agents that act synergistically with said exogenous compounds. In an embodiment, the increase in levels of MAP-2 expression is induced by genetic transformation. Preferably, the cells treated comprise melanocytes.

The method of the invention includes the development kits comprising reagents for performing the methods of the invention. Thus, the invention relates to kits designed to provide a diagnostic or prognostic or screening assay for melanoma which can be implemented by clinical laboratories, health care professionals, or sold commercially for use by individuals without medical supervision. In one aspect the invention comprises a kit for the detection of MAP-2 protein in tumor cells comprising a detection agent which binds to, and complexes with, MAP-2; reagents for detection of the complex; at least one container for packaging the detection agent; at least one container for packaging the reagents; and instructions for use. Preferably, the detection agent comprises antibody to MAP-2 protein.

In another aspect, the invention comprises a kit for the detection of MAP-2 mRNA in tumor cells comprising at least one isolated nucleic acid which hybridizes to MAP-2 mRNA nucleic acid sequences under high stringency conditions; reagents for detection of hybridization; at least one container for said nucleic acid; at least one container for packaging the reagents; and instructions for use. In an embodiment, the kit includes primers for specific amplification of MAP-2 cDNA. Preferably, the isolated nucleic acid that hybridizes to MAP-2 mRNA comprises the nucleic acid sequence complementary to SEQ ID NO: 1 or a fragment thereof. Also preferably, the primers comprise SEQ ID NO: 2 and SEQ ID NO: 3.

Thus, the invention describes that MAP-2 can be detected in tumor cells, and that the level of MAP-2 expression in tumors is inversely correlated with the severity of disease. Referring now to FIG. 1, in an embodiment, invasive melanoma can be stained with an antibody to MAP-2. In melanoma which is a primary melanoma and therefore is not metastatic, strong staining to MAP-2 is detected. Conversely, in melanoma which has acquired the ability to metastasize (or is derived from a metastasis) staining for MAP-2 is not detected.

Microtubule associated proteins (MAPs) are a family of proteins expressed predominantly in neuronal cells (Matus, A., *Ann. Rev. Neurosci.,* 11:29–44 (1988)). MAPs are a heterogeneous group of proteins associated with microtubules, and are known to regulate the stability of microtubules, primarily in axons and dendrites of neurons. MAP-2, one of the most extensively studied MAPs, appears to be expressed only in neurons, and has been used as a marker for neuronal differentiation (Roy, N. S., et al., *Nat. Med.,* 6:271–277 (2000); Encinas M, et al., *J. Neurochem.,* 75:991–1003 (2000); Tojima, T., et al., *Neurosci. Res.,* 37:153–161(2000)). It appears that MAP-2 is localized primarily in dendrites but not in axons.

As defined herein, MAP-2 protein comprises multiple developmentally regulated isoforms which are detected in tumor cells using the methods of the present invention. For example, whereas a high molecular weight (~280 kDa) mature forms MAP-2a and -2b have been shown to persist throughout the life of the neuron, the alternatively spliced juvenile isoform (~70 kDa) MAP-2c appears during different stages of development, diminishing in adult neurons (Garner, C. C., et al.,*J. Cell. Biol.* 106:779–783 (1988)), and the different isoforms have been reported to induce distinct patterns of outgrowth (Leclerc, N., et al., *Mol. Biol. Cell,* 7:443–55 (1996)).

Also as defined herein, MAP-2 mRNA comprises functional transcripts of MAP-2 mRNA such as, but not limited to, the full length mRNA, splice variants, and fragments thereof, such as MAP-2 mRNA sequences comprising GenBank accession numbers NM 002374, and XM 002387.

The tumor cells tested for MAP-2 expression may comprise tissue derived from the neural crest including, but not limited to, spinal tissue and autonomic ganlia, glial cells of the peripheral nervous system, neuroendocrine cells such as chromaffin cells, haemopoetic cells, and melanocytes (see e.g., Le Douarin, N. M:, *The Neural Crest,* Cambridge University Press (1982)). The tumor cells in small cell lung carcinoma are derived from the neural crest and may be similarly be tested for MAP-2 expression.

For example, neoplastic melanocytes exhibit differentiation characteristics found in neural crest derivatives. Also, it has been shown that some benign nevus cells that migrate into the dermis bear a morphological resemblance to Schwann cells of the peripheral nervous system (Reed, J. A., et al., *Am. J. Pathol.* 155:549–55 (1999)), and that desmoplastic (neurotropic) melanomas, which arise most often in sun-damaged skin, share several characteristics of peripheral nerve sheath tumors, including nerve involvement and expression of neural protein markers (Sangueza, O. P., et al., *Am. J. Dermatopathol.,* 20:89–102 (1998)). Other studies have shown expression of neuron-associated markers such as intermediate filament protein peripherin, neuropeptide substance P, muscarinic acetylcholine receptors, and neuron specific enolase in primary and metastatic melanomas (Prieto, V. G., et al., *J. Cutan. Pathol.,* 24:145–50 (1997); Khare, V. K., et al., *J. Cutan. Pathol.,* 25:2–10 (1998); Lammerding-Koppel M., et al., *J. Cutan. Pathol.,* 24:137–44 (1997); Dhillon, A. P., et al., *Histopathol.,* 6:81–92 (1982)). These observations suggest that neural crest derived tissue maintains plasticity of differentiation, and that neoplastic transformation may allow for differential characteristics expression of specific genes associated with neural crest derivatives.

Tumor progression, as used herein, refers to any event which promotes the transition of a non-neoplastic cell into a neoplastic cancerous cell. This can include events which bring about the transition from a pre-neoplastic state to a neoplastic state, wherein a neoplastic state is characterized primarily by unhindered cell proliferation. This can also include the transition of a tumor cell to a metastatic state. As used herein, a metastatic state includes, but is not limited to, unhindered cell proliferation and invasion of distant tissue.

In one aspect, the invention comprises a method for detecting MAP-2 in tumor cells comprising obtaining a sample comprising tumor cells, exposing the sample under high stringency conditions to an isolated nucleic acid that hybridizes to MAP-2 mRNA, and determining the levels MAP-2 mRNA based on said hybridization of said nucleic acid. In an embodiment, MAP-2 mRNA is defined by the sequence deposited to in the GenBank database as accession numbers NM 002374, and XM 002387. In an embodiment, the nucleic acid which hybridizes to MAP-2 mRNA comprises SEQ ID NO: 1 (FIG. 2) or sequence substantially homologous thereto.

Detection of MAP-2 transcript levels may be done by methods standard in the art such as, but not limited to hybridization, reverse-transcriptase polymerase chain reaction (RT-PCR), and Northern blotting of polyA$^+$ RNA or total RNA. Generally total RNA or poly-A+ RNA enriched in mRNA, can be isolated from tissue using methods which are known in the art (see e.g., Ausubel, F. M. et al., eds., 1987–1993, *Current Protocols in Molecular Biology,* John Wiley and Sons, Inc.; U.S. Pat. No. 4,843,155).

In an embodiment, the invention comprises detection of MAP-2 sequences by hybridization. In this embodiment, the invention includes the use of nucleic acid molecules that have substantial homology to, and thus hybridize to the sequence of MAP-2 mRNA. Hybridization conditions can be described as ranging from low to high stringency. Generally, highly stringent conditions refer to washing hybrids in low salt buffer at high temperatures. For example, a high stringency wash may comprise washing in 6×SSC/

0.05% sodium pyrophosphate at 37° C. for a 14 base oligonucleotide, or at 48° C. for a 17 base oligonucleotide, or at 55° C. for a 20 base oligonucleotide, or at 60° C. for a 25 base oligonucleotide, or at 65° C. for a nucleotide probe about 450 nucleotides in length such as SEQ ID NO: 1. Hybridization may be to filter bound DNA using hybridization solutions standard in the art such as 0.5M NaHPO$_4$, 7% sodium dodocyl sulfate (SDS), 1 mM EDTA at 65° C., and washing in 0.1×SSC/0.1% SDS at 68° C. (see e.g. Ausubel, F. M. et al., *Current Protocols in Molecular Biology*, Vol I, Green Publishing Associates, Inc., and John Wiley & Sons, N.Y.). Nucleic acid probes may be labeled with radionucleotides by end-labeling with, for example, [γ-$^{32}$P]ATP, or incorporation of radiolabeled nucleotides such as [α-$^{32}$P] dCTP. Alternatively, probes may be labeled by incorporation of biotinylated or fluorescein labeled nucleotides, and the probe detected using antibodies to the label.

Substantial homology in the nucleic acid context means that the sequences of interest, or their complementary strands are the same when aligned, with in some cases deletions and insertions, in at least 60% of the nucleotides, and more preferably at least about 70% of the nucleotides, and more preferably at least about 80% of the nucleotides, and more preferably at least about 90% of the nucleotides, and even more preferably at least about 95% of the nucleotides.

For certain applications, mRNA is used as a template to generate MAP-2 cDNA. For example, for quantitation of mRNA by RT-PCR, total or poly-A$^+$ RNA is reverse transcribed using oligo-dT primers, wherein dT is defined as deoxythymidylate. For increased specificity, the primer may is designed with 3' end which specifically hybridizes to MAP-2 mRNA. Thus, in an embodiment, the method also includes the steps of: (a) preparing MAP-2 cDNA mRNA isolated from said test sample as a template; (b) conducting polymerase chain reaction (PCR) amplification using primers specific for the MAP-2 gene comprising amplification conditions such that a PCR product is generated in cells comprising MAP-2 mRNA but not in cells which do not comprise MAP-2 mRNA; and (c) detecting the MAP-2 specific PCR product.

Techniques for detection of amplified sequences include gel electrophoresis of the amplified DNA and visualization of the amplified product by ethidium bromide staining or hybridization of a radiolabeled probe which recognizes (i.e. is homologous to) the amplified DNA. Alternatively, the amplified DNA may be labeled by incorporation of oligonucleotide primers which have been end-labeled with a detectable chemical moiety such as, for example, biotin or fluorescein, or by incorporation of radiolabeled nucleotides or nucleotides labeled with a detectable chemical moiety such as, for example, fluorescein-dUTP, and the like. The chemically labeled products are then detected using reagents specific for that moiety.

For example, RT-PCR may be performed using cell RNA and primers comprising biotinylated primers specific to sequences comprising MAP-2 cDNA. The amplified DNA may then be blotted to a solid support, and detected using streptavidin labeled IgG and a secondary anti-IgG antibody labeled with an enzyme, such as alkaline phosphatase, which comprises a calorimetric reaction product. Thus, the presence of the colored product provides a quantitative assay for the presence of cDNA (and thus the presence of mRNA template) in the sample.

In another embodiment, the nucleic acid that hybridizes to MAP-2 mRNA (or cDNA) is arranged as microchip or an array. In this manner, hybridization of MAP-2 specific PCR products may be detected by hybridization of the PCR product to the array, as for example by labeling the PCR product with a moiety which comprises an electrochemical, luminescent, ultraviolet, and/or fluorescent signal.

In another embodiment, differential expression of MAP-2 is detected by differential display. For example, MAP-2 mRNA transcripts specific to melanoma cells are detected by differential display. It has been shown that treatment of cultured human metastatic melanoma cells with the growth inhibitor hexamethylene bisacetamide (HMBA) inhibits growth, causes selective down-regulation of the melanocyte-differentiation marker TYRP1 (Fang, D. et al., *Biochem. Biophys. Res. Commun.*, 256:657–63 (1999); Vijayasaradhi, S., et al., *J. Invest. Dermatol.*, 105:113–9 (1995)), and results in the formation of dendrite-like structures (FIG. 3). Differential display with primers P4 (5'-ATTAACCCTCACTAAATGCTGGTAG) (SEQ ID NO: 4) and the T7 primer (5'-CATTATGCTGAGTGATATCTTTTTTTTTGA-3') (SEQ ID NO: 5) generates an approximately 450 bp cDNA which displays 98% identity to the 3'-untranslated region in exon 19 of MAP-2 cDNA in HMBA-treated (i.e. growth inhibited) metastatic melanoma cells, but not in untreated metastatic melanoma cells.

MAP-2 expression may also be detected by Northern analysis. Northern analysis generally comprises identification of specific RNA molecules in total or polyA$^+$ RNA by hybridization with probes homologous to sequences of interest. For Northern analysis, individual RNA molecules are separated from each other based primarily on size by electrophoresis through molecular sieve gels comprising agarose, acrylamide and the like. After electrophoresis, the separated RNAs are transferred to a membrane such as, but not limited to, nitrocellulose or Nytran (Schleicher & Schuell, Keene, N. H.), and individual RNAs identified by hybridization of the membrane to nucleic acid probes homologous to the RNA of interest.

Figure 4:
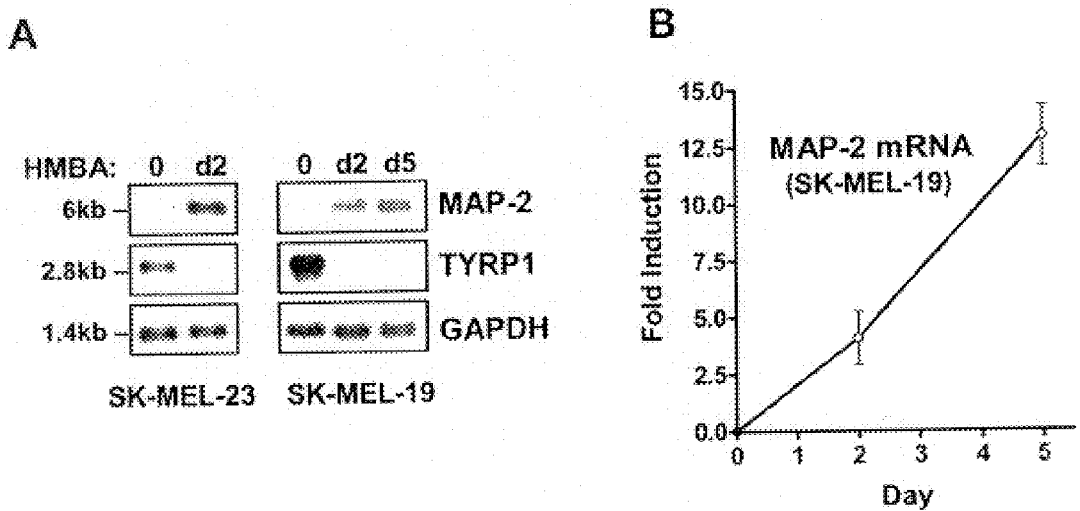
FIG. 4 shows an aspect of an embodiment of the invention comprising up-regulation of MAP-2 mRNA in SK-MEL-19 and SK-MEL-23 (cl.22) metastatic melanoma cells by treatment with HMBA for 2 to 5 days as measured by (A) Northern blot analysis of polyA$^+$ RNA probed with $^{32}$P-labeled probes homologous to MAP-2, tyrosinase-related protein 1 (TYRP1) or glyceraldehyde-3-phosphate dehydrogenase (GAPDH), or (B) quantitative analysis of MAP-2 mRNA induction in SK-MEL-19 cells where band intensities were measured, normalized to GAPDH, and plotted as mean relative intensities±SEM from 3 independent experiments.

For example, and referring now to FIG. 4, poly-A$^+$ RNA isolated from human metastatic melanoma cells was probed with a radiolabeled probe generated from a ~450-bp MAP-2 cDNA fragment identified by differential display. It was found that metastatic melanoma cells have low levels of MAP-2 mRNA (FIG. 4A). In contrast, metastatic cells treated with the differentiation inducing agent HMBA show an approximately 4-fold increase in the MAP-2 mRNA after 2 days, and a 12-fold increase in MAP-2 after 5 days.

For some applications, it may be preferable to measure protein, as opposed to transcript levels of a MAP-2 in tumor cells. Thus, in one aspect, the invention comprises a method for detecting MAP-2 in a sample comprising tumor cells comprising the steps of obtaining a test sample comprising tumor cells; disrupting the cellular membrane of the cells to allow access to intracellular proteins; incubating the cell proteins with a detection agent which recognizes and forms a complex with MAP-2 protein or fragments thereof; and detecting the presence of the complex. The tumor cells may comprise tissue derived from the neural crest, such as melanoma cells, and the like.

The invention comprises measuring all MAP-2 isofoms as well as proteins with substantial homology thereto. The terms "substantially homologous" when referring to polypeptides refer to at least two amino acid sequences which when optimally aligned, are at least 75% homologous, preferably at least about 85% homologous, more preferably at least about 90% homologous, and still more preferably 95% homologous. Optimal alignment of sequences for aligning a comparison may be conducted using the algorithms standard in the art (e.g. Smith and Waterman, *Adv. Appl Math.* 2:482 (1981); Needleman and Wunsch, *J. Mol. Biol.* 48:443 (1970); Pearson and Lipman, *Proc. Natl. Acad. Sci. (USA)*, 85:2444 (1988)) or by computerized versions of these algorithms (Wisconsin Genetics Software Package Release 7.0, Genetics Computer Group, 575 Science Drive, Madison, Wis.).

The invention comprises methods for measuring MAP-2 protein which are known in the art. Generally, any method used to detect a complex of MAP-2 protein, or a fragment thereof may be used. Generally, the formation of a complex involves allowing MAP-2 to interact with a binding partner and then measuring the formation, or lack of formation, of such a complex. Thus, a detection agent is any composition that can be used to detect MAP-2 protein by interacting with the protein. Complex formation may be measured in solution, or by allowing the complex to bind to a solid surface. The invention comprises chemical, biological, physical, electrochemical and similar means to measure the interaction of MAP-2 protein with the detection agent. For example, MAP-2 protein may be identified and quantified by methods known in the art such as, but not limited to, staining of thin sections, immunoblot analysis, sandwich assays, solution enzyme-linked immunoassay (ELISA), radioimmunoassay (RIA), and the like. Other techniques include quenching of a label on one of the binding partners (e.g. U.S. Pat. No. 4,109,496) or the use of MAP-2 tagged with an affinity agent which allows for binding of MAP-2 ligand to a solid surface, for measurement of complex formation.

As used herein, a carrier, solid surface, or solid phase support is a surface which is capable of immobilizaing cells, cell particles or soluble proteins. The support can be washed with suitable buffers to remove non-bound components, and can be incubated with protein solutions to block non-specific binding sites. Well-known solid phase supports include glass, polypropylene, dextran, nylon, modified celluloses, polyacrylamides, and the like. Included as solid surfaces for binding reactions are microtiter wells, filter arrays, beads, dip-sticks and other suitable agents for binding assays.

For example, in the well-used approach of an enzyme linked immunoassay (ELISA or EIA) (see e.g. Voller et al., *Diagnostic Horizons* 2:1–7 (1978)) an enzyme bound to an antibody will react with a chromogenic substrate to produce a product which can be detected, as for example by spectroscopic, fluorometric, or visual means. Enzymes which can be used to label the antibody for production of a detectable signal include alkaline phosphatase, horseradish peroxidase, glucose oxidase, catalase, glucose-6-phosphate dehydrogenases, and the like.

Alternatively, detection may employ radiolabeling the antibody as for example in the approach of a radioimmunoassay (RIA) and the amount of antibody bound measured using a scintillation counter, a gamma counter, or by autoradiography. In another embodiment, the antibody is labeled with a fluorescent compound such as fluorescein isothiocyanate, rhodamin, phycoerythrin, phycocyanin, fluorescamine and the like.

MAP-2 protein may be detected in-situ, as for example by staining of tissue biopsies. Staining of thin sections generally comprises methods standard in the art as those discussed in the Examples herein. The invention also contemplates injecting radiolabeled antibody to MAP-2 (or a similar binding agent which is labeled in some manner to allow for detection) into a patient for detection of MAP-2 staining in tissues of interest.

Immunoblotting generally comprises separation of proteins primarily by molecular weight by sodium dodecyl sulfate polyacrylamide gel electrophoresis (SDS-PAGE) and transfer of the separated proteins to a membrane. Proteins of interest can then be detected by exposing the membrane to an antibody to the protein(s), and detecting the formation of immune complexes by methods standard in the art, as for example by ELISA. The formation of an immune complex between the protein immobilized on the membrane and the antibody specific to a protein of interest may then be detected by assaying for the reaction catalyzed by the antibody bound enzyme.

Alternatively, binding may be measured using microtiter wells or other types of reaction vessels. For example, microtiter wells may be pre-coated with antibody to MAP-2 and a mixture comprising radiolabeled MAP-2 and a homogenate from the sample of interest added. In this approach, binding of radiolabeled MAP-2 to the microtiter wells is displaced in a quantitative manner by increasing amounts of MAP-2 in the sample.

Alternatively, the assay may employ a dip-stick approach suitable for development as a kit. Thus, an assay kit for detection of MAP-2 protein may comprise a dip-stick coated with a known amount of MAP-2 protein and an enzyme-labeled antibody which specifically recognizes MAP-2, such as alkaline phosphatase labeled M13 antibody. The assay would be designed such that a sample comprising MAP-2 protein in solution would compete for binding of the antibody to the MAP-2 protein on the dip-stick. Thus, a sample comprising high levels of MAP-2 would comprise less color on the dip-stick than a sample with little or no MAP-2.

Antibodies may be commercially available, or may be prepared by methods standard in the art. Thus, antibodies may include, but are not limited to, polyclonal antibodies, monoclonal antibodies (mAbs), single chain antibodies, Fab fragments, chimeric antibodies, epitope-binding fragments and the like. For example, polyclonal antibodies are a heterogeneous population of antibody molecules derived from the sera of animals immunized with the antigen of interest. Adjuvants such as Freund's (complete and incomplete), peptides, oil emulsions, lysolecithin, polyols, polyanions and the like may be used to increase the immune response. Thus, in an embodiment, polyclonal antibody to MAP-2 is prepared by injection of MAP-2 supplemented with an adjuvant using methods known in the art.

Monoclonal antibodies are homogeneous populations of antibodies to a particular antigen, and are generally obtained by any technique which provides for production of antibody by continuous cell lines in culture (see e.g. U.S. Pat. No. 4,376,110). Monoclonal antibodies may be humanized, to thereby reduce interaction with unrelated epitopes by the technique of single chain antibodies (see e.g. U.S. Pat. No. 4,946,777 and Bird, *Science* 242:423–426 (1988)).

The invention describes that MAP-2 expression is reduced in tumors having high metastatic potential as compared to tumors from the same tissue which have low metastatic potential. For example, and referring to FIGS. 4 and 5, MAP-2 is detected in primary melanoma cell types such as a radial growth phase melanoma (WM35) and some types of vertical growth phase melanoma (WM75). In contrast, MAP-2 mRNA is much lower (or is not detected at all) in WM98-1 vertical growth phase melanoma cells isolated from a patient who had a 5 year recurrance, WM451 metastatic melanoma cells or in SK-MEL-19 metastatic melanoma cells. Also, as shown in FIG. 3, MAP-2 mRNA is low in metastatic melanoma cells, but increases when such cells are treated with the growth inhibitor HMBA. Thus, cultured cells comprising melanoma cells which have increased potential to metastasize have decreased expression of MAP-2 as compared to cultured cells comprising lower metastatic potential.

Also, FIG. 6 illustrates a Western blot comprising detergent extracts of melanoma cell lines probed with HM-2 monoclonal antibody. Consistent with patterns seen for MAP-2 mRNA, the 280 kDa band corresponding to the mature MAP-2a, 2b isoform is detected in WM35 cells and WM75 cells, but not in WM115 cells, WM 793 cells or SK-MEL-19 cells. The 70 Kda MAP-2 isoform is detected in WM35 cells, WM75 cells, WM115 cells and faintly (over background) in SK-MEL-19 cells.

Thus in an embodiment, the invention comprises a method for determining the metastatic potential of a tumor sample comprising the steps of obtaining a test tumor sample of unknown metastatic potential from a subject; determining the level of MAP-2 expression in the test sample; and assessing the metastatic potential of the sample based on the level of MAP-2 expression in the test sample relative to a non-metastatic control comprising cells of the same or a similar tumor type.

For example, invasive melanoma cells comprising high levels of MAP-2 represent cells which have not yet acquired the ability to metastasize. In contrast, invasive melanoma cells comprising little to no MAP-2, are associated with an increased potential for metastatic disease. Thus in an embodiment, the invention comprises obtaining a tissue sample comprising an invasive melanoma; staining the invasive melanoma for MAP-2 protein; and assessing the metastatic potential of the melanoma based on the degree of staining for MAP-2. In this case strong staining for MAP-2 in the invasive melanoma is associated with cells which have not acquired the potential to metastasize, whereas the presence of regions of the tumor which do not stain for MAP-2 is associated with tumor cells which have increased potential to metastasize.

In some cases the step of obtaining an invasive melanoma includes histochemical evaluation of a tissue sample as an initial screening to distinguish invasive melanoma from in situ melanoma and nevi. Also, staining for MAP-2 may comprise immunohistochemistry using an antibody such as M13, that specifically recognizes and binds to the mature 280 kDa forms of MAP-2 protein, MAP-2a and MAP-2b, or to an antibody such as HM-2, that recognizes and binds to the 280 kDa mature forms of MAP-2 protein, MAP-2a and MAP-2b, and the 70 kDa juvenile form of the MAP-2 peptide.

For example, referring now to FIG. 7, the inverse correlation between MAP-2 expression and metastatic potential can be detected by in situ immunohistochemical staining of biopsy tissue. As shown in FIG. 7A, in a malignant melanoma arising in a nevus, the dermal nevus cells and the cells within the primary melanoma show cytoplasmic staining for MAP-2. More importantly, in cutaneous primary melanomas showing extensive invasive components, a majority of the invasive component is strongly positive for MAP-2 (FIG. 7B). In contrast, metastatic lesions excised from the left arm and brain from the same patient show negative or weakly positive staining, respectively. Also, as shown in FIG. 7C, MAP-2 staining in metastatic melanoma is heterogeneous, with a few cells and/or small clusters showing intense cytoplasmic staining, while adjacent cells are devoid of MAP-2. Whereas a majority of nevi and many primary melanomas are strongly MAP-2 positive, only a small percentage of metastatic melanomas have foci of MAP-2 stained cells, and most metastatic specimens may show only focal or weak heterogeneous expression (Table I).

In some situations, it is useful to determine the origin of a tumor, as well as whether the tumor is a primary tumor or a metastasis. For example, because primary melanomas display different MAP-2 staining than metastases, the differential staining of tumors for MAP-2 may also be used to determine if a melanoma is a primary tumor or a metastasis. Also, in some situations it is valuable to determine whether or not a lesion has metastatic potential, even without fully characterizing the nature of the growth. For example, in some situations it can even be difficult to resolve melanocytic nevi from: (a) a melanoma which has metastasized to the skin; (b) a melanoma that histologically simulates a nevus; (c) a nevus that histologically simulates a melanoma; or (d) some other neural crest-derived tumor. Thus, the invention comprises a method for identifying whether an abnormal lesion is benign or potentially malignant comprising the steps of: (a) isolating tissue comprising the lesion; (b) staining for MAP-2 protein; and (c) assessing whether the lesion is benign or potentially malignant based on the degree of staining for MAP-2, wherein a strong staining for MAP-2 is associated with a benign lesion and lack of staining for MAP-2 is associated with a lesion that is potentially malignant.

In one aspect, the invention describes methods for identifying compounds that modulate MAP-2 levels in cells. Cells which can be used in such assays include any cell with a capability of MAP-2 expression. Preferably, the assay would employ tumor cells such as melanoma tumor cell lines WM35, WM95, WM115, and SK-MEL-19 or SK-MEL-23, and the like. Also preferably, the assay may employ other tumor cells of neural crest origin. In addition, purified primary tumor cells may be used, as well as recombinant, transgenic cell lines comprising expression of MAP-2 under a regulatory promoter.

In one aspect, the invention comprises a method for screening for compounds that modulate MAP-2 expression comprising: incubating cells with a compound of interest; disrupting the cellular membrane of the cells to allow access to intracellular proteins; incubating the cell proteins with a detection agent which recognizes and complexes with MAP-2 protein or fragments thereof; detecting the presence of the complex; and comparing the levels of MAP-2 protein in cells treated with the compound of interest to the levels of MAP-2 protein in tumor cells not incubated with the compound of interest. Alternatively assays may measure MAP-2 mRNA or cDNA. Compounds that may modulate MAP-2 expression include, but are not limited to, cytokines (e.g. TPA), organics (e.g. HMBA), peptides or proteins (e.g. growth factors; cholera toxin), amino acids (e.g. D or L amino acids, phosphopeptides); peptidomimetics; and the like. Alternatively, assays may be performed by transfection of cell lines of interest using standard techniques (see e.g. Ausubel et al., 1989) and cells evaluated for expression of the sequence of interest, as for example by measuring protein production.

In that expression of MAP-2 is strongest in primary tumors, with a decrease as cells progress to later stages of cancer, MAP-2 may be used to prevent early stage tumors from progressing to later stage diseases. Thus, in another aspect, the invention comprises a method to prevent tumor progression comprising increasing levels of MAP-2 expression in cells. In an embodiment, the method comprises increasing MAP-2 protein levels. In an embodiment, the method comprises increasing MAP-2 mRNA levels.

Thus, in an embodiment, expression of MAP-2 during terminal differentiation of dermal nevus cells leads to microtubule stabilization with consequent withdrawal from the cell cycle and either senescence or apoptosis. Microtubules and other cytoskeletal elements play critical roles in diverse cellular processes including having effects on cell motility, signal transduction and mitosis (Kobayashi, N., et al., *Cell Tissue Res.*, 291:163–174 (1998)). For example, phosphorylation-regulated association of MAP-2 isoforms with intracellular signaling proteins such as Src and Grb2, has recently been demonstrated, and may play a role in modulation of neuronal cytoskeleton by extracellular signals (Lim, R. W. L., et al., *J. Biol. Chem.*, 275:20578–20587 (2000)). Anticancer agents may act by inhibiting microtubule formation (e.g. vinca alkaloids, podophyllotoxin, cochicine, methoxy and ethoxy substituted 3-aroyl-2-arylbenzo[b]thiophenes), or by promoting the formation of highly stable microtubules (e.g. taxol and taxol derivatives). Treatment with such compounds apparently leads to an inability of the cell to pass through the G2 and M phases of the cell cycle due to an inability of these cells to form competent mitotic spindals (see e.g. U.S. Pat. Nos. 6,080,777; 5,922,775; 5,597,830; 6,162,930; and 6,150,398).

In an embodiment, the increase in MAP-2 is induced by exogenous compounds, such as HMBA and the like. HMBA is a hybrid polar compound which has been shown to induce terminal differentiation in mouse erythroleukemia cells (MEL) and a variety of human tumor cells (Rilkind, R. A., et al., *Pharmacol. Ther.*, 69:97–102 (1996), and causes accumulation of cells in $G_0/G_1$ phase with a significant decrease in population of cells in $G_2/M$ phase. Although the exact mechanism(s) by which HMBA induces differentiation are not known (Aouani, A., et al., *Hormone Metabolic Res.*, 31:402–5 (1999); Leng, L., et al., *Cancer Res.*, 53:5554–8 (1993); Richon, V. M., et al., *Proc Natl Acad Sci U.S.A.*, 95:3003–7 (1998); Scheele, J. S., *Mol. Cell. Biochem.* 185:55–63 (1998)), cAMP-dependent protein kinase A and protein kinase Ce have been implicated in the mechanism of HMBA action.

Figure 8:
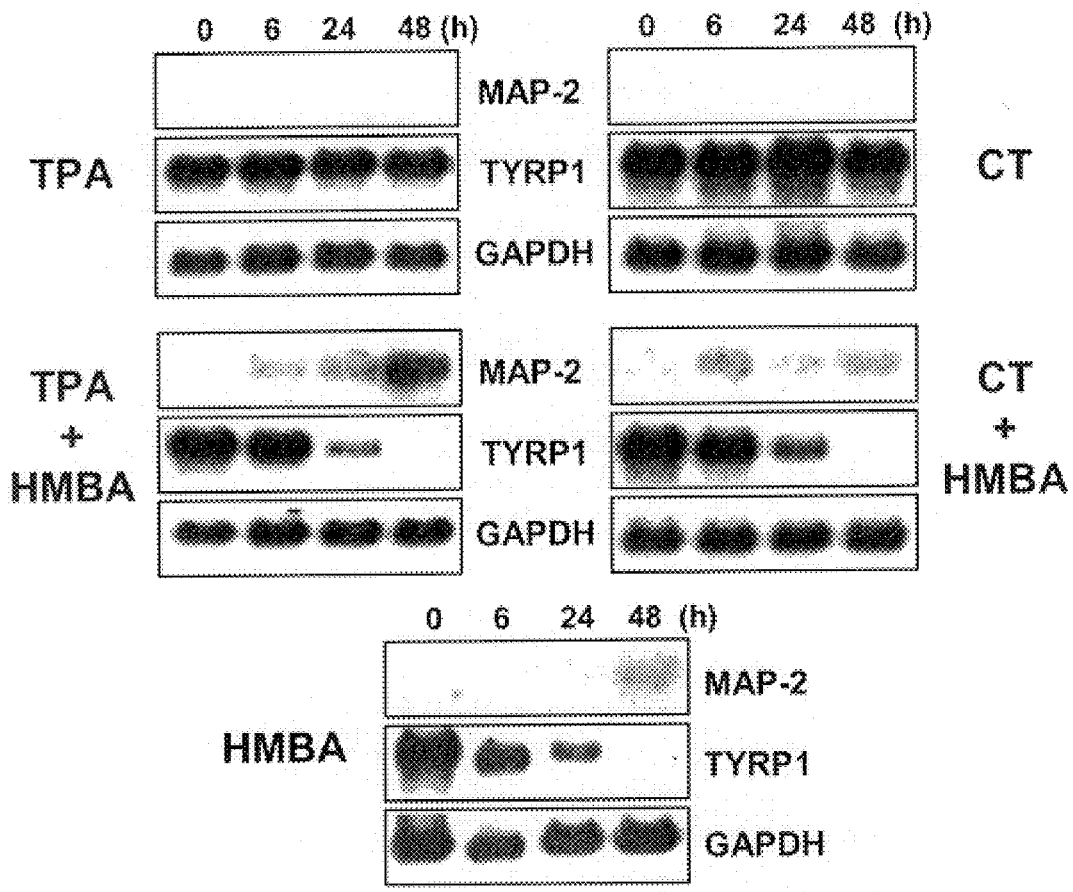
FIG. 8 shows an aspect of an embodiment of the invention comprising the role of cAMP and protein kinase C signaling pathways in up-regulation of MAP-2, wherein SK-MEL-19 melanoma cells were treated with either 5 mM HMBA, 2.5 nM cholera toxin (CT), 10 ng/ml of the phorbol ester 12-O-tetradecanoyl phorbol-13-acetate (TPA), a combination of the above amounts of HMBA and CT, or of HMBA and TPA, for 6, 24 and 48 hours (h) as indicated, and 10 ug total RNA/lane electrophoresed and blotted for Northern analysis wherein blots were hybridized sequentially with $^{32}$P-labeled MAP-2, TYRP1 and GAPDH probes.

The present invention also contemplates possible synergy between MAP-2 and other modulators of cell function. For example, the effects of MAP-2 binding to microtubules can be accentuated by compounds that stimulate microtubule formation or facilitate MAP-2 binding. MAP-2 induction may be regulated by other cell signaling mechanisms as well. For example, activators of cell signaling pathways include phorbol ester 12-O-tetradecanoyl phorbol-13-acetate (TPA), cholera toxin (CT), and the like. Other regulators of the cell cycle check point might be expected to play a role as switch points for choosing between cell proliferation and apoptosis. For example, apoptosis can be induced by exposing cells to diptheria toxin or pseudomonas toxin, or inhibited using cellular proteins (see e.g. U.S. Pat. No. 6,156,564). Referring now to FIG. 8, treatment of primary melanoma cells with TPA alone or cholera toxin alone does not change MAP-2 expression in metastatic melanoma cells. When HMBA is added together with TPA or CT, however, significant increases in MAP-2c mRNA are seen as early as 6 h after treatment. Thus, activators of cell signaling pathways may facilitate induction of MAP-2 in response to growth inhibition.

The therapeutic efficacy of exogenous compounds can be determined by standard pharmaceutical procedures in cell cultures or experimental animals using procedures known in the art. The dose ratio between toxic and therapeutic effects is the therapeutic index and may be expressed as $LD_{50}/ED_{50}$. Generally, compounds which exhibit large therapeutic indices are preferred. Administration of the compound may be hourly, daily, weekly, monthly, yearly or a single event. Preferably, the effective amount of the compound comprises from about 1 ng/kg body weight to about 100 mg/kg body weight. More preferably, the effective amount of the compound comprises from about 1 ug/kg body weight to about 50 mg/kg body weight. Even more preferably, the effective amount of the compound comprises from about 10 ug/kg body weight to about 10 mg/kg body weight. The actual effective amount will be established by dose/response assays using methods standard in the art. Thus, as is known to those in the art, the effective amount will depend on bioavailability, bioactivity, and biodegradability of the compound.

In an embodiment, the subject is a human. Preferably, the subject is suffering from cancer. More preferably, the cancer is of a tissue derived from the neural crests such as, but not limited to, melanoma, neuroblastoma, gliomas, and small cell lung cancer.

Administration of the compound may be by intralesional, intraperitoneal, intramuscular, or intravenous injection. Alternatively, the compound may be administered by infusion or liposome-mediated delivery. Also, administration of the compound may include oral, sublingual, or nasal delivery, or by topical application to the skin.

Preferably, administration of the compound includes a pharmaceutically acceptable carrier such as a diluent, liposome, microcapsule, a polymer encapsulated cell, a virus or other carriers known in the art. For example, tablets or capsules may utilize pharmaceutically acceptable binding agents (e.g. polyvinylpyrrolidone, hydroxypropyl methylcellulose, starch); fillers (e.g. lactose, microcrystalline cellulose, calcium hydrogen phosphate); and lubricants (e.g. magnesium stearate, silica or talc). Liquid preparations for oral administration may comprise syrups or suspensions prepared by conventional means with pharmaceutically acceptable additives such as suspending agents (e.g. hydrogenated fats, sorbitol syrup); emulsifying agents (e.g. lecithin) and preservatives. Preparations may contain buffer, salts, and flavoring agents as appropriate. Similarly topical administration may be by means of a gel, or cream with solvents, such as DMSO to increase uptake into the skin.

The invention also includes recombinant vectors for production of MAP-2 and or agents that modify MAP-2 and can therefore be used as cancer therapeutics. Thus, the invention encompasses (a) DNA vectors that include (i) MAP-2 sequences or (ii) the DNA sequences of agents which may influence levels of MAP-2 in cells; (b) DNA expression vectors that contain (i) MAP-2 sequences or (ii) the sequences of agents that may influence the levels of MAP-2 associated with a regulatory element that directs expression of the coding sequences; and (c) genetically engineered host cells that contain (i) MAP-2 sequences or (ii) the sequences of agents that may influence the levels of MAP-2 with a regulatory element regulatory element that directs expression of the coding sequences in the host cells.

The invention also includes production recombinant forms of MAP-2 and agents that influence levels of MAP-2 in cells in large scale for therapeutic formulations. Methods which are well known to those in the art can be used to construct expression vectors containing the sequences of interest (see e.g. Maniatis et al., *Molecular Cloning: A Laboratory Manual*, Cold Spring Harobor Laboratory, and Asubel et al., 1989)). Thus, a variety of host-expression vector systems may be utilized including, but not limited to bacterial systems such as bacteriophages, plasmids or cosmid expression vectors; yeast recombinant expression vectors; insect cell systems (e.g. baculovirus); or mammalian cell systems such as COS, CHO, 3T3 cell lines harboring recombinant expression constructs containing mammalian promoters (e.g. metallothionein promoter) or viral promoters (e.g. adenovirus late promoter).

For example, in the insect system, *Autographa californica* nuclear polyhedrosis virus (AcNPV) is used as a vector to express foreign genes. The virus is grown in *Spodoptera frugiperda* cells, or the like. The gene of interest (e.g. MAP-2 or molecules that influence the levels of MAP-2) is cloned into a non-essential region of the viral genome and placed under control of a viral promotor, such as the promoter for the polyhedrin gene. Commercial vectors and expression systems are currently available (e.g. Clontech, PaloAlto, Calif.).

In mammalian systems, a number of viral based systems can be utilized. For example, where adenovirus is used as the expression vector, the gene of interest may be ligated to an adenovirus transcription/translation control element, such as but not limited to the late promoter and tripartite leader sequence. The construct is then inserted into the adenovirus genome to produce a recombinant virus that is capable of expressing the sequence of interest (see e.g. Logan et al, *Proc. Natl. Acad. Sci. (USA)* 81:3655–3659 (1984); Bittner et al., *Methods in Enzymol.* 153:516–544 (1987)).

The invention includes the use of genetic modification of cells as a method to modify MAP-2 expression. In an embodiment, the increase in MAP-2 is induced by gene replacement therapy. Preferably, the cells treated comprise melanocytes. In this approach, one or more copies of the MAP-2 gene are inserted into melanocytes using vectors which target these cells including retrovirus vectors, parvovirns vectors, and non-vector delivery techniques such as liposomes, and cationic amphiphiles. Additionally, devices for the delivery of gene therapy compositions to targeted sites, such as catheter systems, or devices for implantation at the tumor site (e.g. U.S. Pat. Nos. 6,135,976 and 5,626,561). Specific examples of gene therapy approaches which may be used in the present invention include, but are not limited to those approaches described in U.S. Pat. Nos. 6,135,976; 5,719,131; 5,714,353; 5,656,465; 5,626,561; 5,399,346; 5,334,761; 5,283,185; 5,264,618; 5,252,479; and 4,394,448, each of which are incorporated herein by reference in their entirety.

Features and advantages of the inventive concept covered by the present invention are illustrated in the following examples. The following materials and methods were utilized in the examples described herein.

EXAMPLES

Example 1

Cell Culture.

Primary cultures of human melanocytes were initiated from neonatal foreskins. Fresh skin specimens were washed three times with Hanks' Balanced Salt Solution (HBSS) and excess fat removed. Samples were cut into small pieces and incubated in 0.25% trypsin solution at 4° C. overnight. The epidermis was separated from the dermis and epidermal cells suspended and cultured in Ham's F10 nutrient medium with 10% FBS (fetal bovine serum), 85 nM 12-O-tetradecanoylphorbol-13-acetate (TPA), 0.1 mM 3-isobutyl-1-methylxanthine (IBMX), 2.5 nM cholera toxin (CT) and 100 µg/ml geneticin.

Primary human melanoma cell lines (WM75, WM35, WM98-1, WM115 and WM793) and metastatic human melanoma cell lines (WM45 1) were provided by Dr. Meenhard Herlyn (Wistar Institute, Philadelphia, Pa.). WM35 is derived from an early-stage radial growth phase (RGP) primary lesion (Breslow thickness 0.69 mm, Clark level II) from a patient who was cured. It has been shown that WM35 cells do not metastasize in nude mice (Elder, D. E., et al., *Cancer Res.*, 49:5091–5096 (1989)). WM75 is derived from vertical growth phase (VGP) primary melanoma (Breslow thickness 6.25 mm, Clark level IV) from a patient who had a subsequent metastatic lesion. WM98-1 is derived from a VGP primary melanoma (Breslow thickness 5.4 mm, Clark level) where the patient had a recurrence of melanoma during 5-year clinical follow-up. WM98-1 is tumorigenic in nude mice (Rodeck U., et al., *Int. J. Cancer,* 40:687–690 (1987); Satyamoorthy K., et al., *Melanoma Res.,* 7:S35–42 (1997)). WM115 is derived from a VGP primary melanoma (Breslow thickness 2.24 mm, Clark level III) in a patient who had recurrences 9 months later (Satyamoorthy K., et al., *Melanoma Res.,* 7:S35–42 (1997)). WM793 is derived from a VGP primary melanoma (Breslow thickness 0.55 mm, Clark level II) in a patient who did not have recurrences during a 10 year follow-up (Satyamoorthy K., et al., *Melanoma Res.,* 7:S35–42 (1997)). The WM cell lines were grown in Ham's F10 medium containing 10% FBS and 1% antibiotic-antimycotic mixture.

Metastatic melanoma cell lines SK-MEL-19, SK-MEL-23 clone 22 (cl. 22) (Houghton, A. N., et al., *J. Exp. Med.,* 165:812–829 (1987); Carey, T. E. et al., *Proc. Natl. Acad. Sci., USA,* 73:3278–3282 (1976)), were grown in MEM medium supplemented with 10% FBS, 1% antibiotic-antimycotic mixture, 1% nonessential amino acids and 1% glutamine. Cells were seeded at a density of $5 \times 10^5$ cells/10 ml culture medium in 100 mm dishes. Culture medium, FBS, HBSS, antibiotic-antimycotic mixture, geneticin, nonessential amino acids and glutamine were purchased from Gibco-BRL (Bethesda, Md.). TPA, IBMX and CT were purchased from Sigma Chemical Co., (St. Louis, Mo.). Hexamethlylene bisacetamide (HMBA) was obtained from Aldrich Chemical Co. (Milwaukee, Wis.).

Example 2

RNA Isolation

Cells grown as monolayers were washed twice with HBSS (Hank's balanced salt solution), harvested by trypsinization, washed once with ice-cold PBS (phosphate buffered saline). Poly A$^+$ RNA and total RNA were isolated from cell pellets using the Micro-FastTrack mRNA (Invitrogen Corp., Carlsbad, Calif.) and Ultraspec™-II RNA isolation systems (Biotecx Laboratories, Inc., Houston, Tex.), respectively. Total RNAs were treated with DNase I (Clontech Laboratories Inc., Palo Alto, Calif.) to remove genomic DNA prior to RT-PCR.

Example 3

Northern Analysis

Northern analysis was performed as described (Fang, D., et al., *Biochem. Biophys. Res. Commun.,* 256:657–63 (1999)) using the Northern Max kit and Strip-EZ DNA probe synthesis and removal kit (Ambion, Inc., Austin, Tex.). Blots were washed at room temperature for 20 min with 2×SSC (17.53 g/L NaCl; 8.82 g/L sodium citrate), 0.5% SDS (sodium dodecyl sulfate), followed by washes at 55–60° C. for 20 min with 0.5%×SSC, 0.5% SDS and then 0.1%×SSC, 0.5% SDS. The cDNA templates for tyrosinase, TYRP1, DCT/TYRP2, and MITF probes were generated as described in Fang, D., et al., (*Biochem. Biophys. Res. Commun.,* 256:657–63 (1999)). The template for the human GAPDH probe was from Ambion Inc., (Austin, Tex.). The human β-actin probe template (838 bp) was amplified using primers from Clontech Laboratories, Inc., (Palo Alto, Calif.) sense: 5'-ATCTGGCACCACACCTTCTACAATGAG CTGCG-3' (SEQ ID NO: 6); and anti-sense: 5'-CGTCATACTCCTGCTTGCTGATCCACATCTGC-3' (SEQ ID NO: 7). The MAP-2 probe detected a major band at approximately 6.0 kb, the tyrosinase probe detected a major band at about 1.9 kb, the TYRP1 probe detected a 2.8 kb band, the DCT/TYRP2 probe detected a 4.5 kb band, the MITF probe detected a 5.5 kb band, the GAPDH 1 probe detected a 1.4 kb band, and the β-actin probe detected a 1.8 kb band. Band intensity was quantified with ImageQuaNT software. The relative intensities for each probe were obtained by normalizing to GAPDH.

Example 4

Identification of MAP-2 Expression in Melanoma Cells by Differential Display (DD) and Northern Analysis Differential display was used to characterize changes in gene expression associated with growth inhibition in melanoma cells. For differential display (DD), RT-PCR was performed using a GeneAmp System 2400 (Perkin-Elmer Corp., Foster City, Calif.). DD was performed using the Delta™ Differential Display Kit (Clontech Laboratories Inc.). First-strand cDNA was synthesized from 2 µg total RNA isolated from 70–85% confluent control or 5 mM HMBA-treated SK-MEL-19 cells using an oligo (dT) primer. Diluted cDNA (1:12.5 and 1:50) was used to amplify DD-PCR product in the presence of [α-$^{33}$P]dATP (Dupont NEN, Boston, Mass.) using a random combination of arbitrary primers and oligo (dT) primers. PCR products were resolved by electrophoresis in a 5% polyacrylamide, 8 M urea sequencing gel. The gel was dried and exposed to Biomax MS film (Kodak, Rochester, N.Y.). Bands differentially expressed between untreated and treated samples were cut, eluted, re-amplified, sequenced by the ABI 377 DNA Sequencer (Perkin-Elmer Corp., Foster City, Calif.).

Differential display analysis was performed using RNA obtained from control and HMBA-treated SK-MEL-19 melanoma cells. Primer P4: ATTAACCCTCACTAAAT-GCTGGTAG (SEQ ID NO: 4) and oligo dT primer T7: CATTATGCTGAGTGATATCTTTTTTTTTGA (SEQ ID NO: 5) (Delta™ Differential Display Kit; Clontech Laboratories Inc.) amplified an approximately 450 bp cDNA that is over expressed in treated cells. Nucleotide sequence analysis of the ~450-bp cDNA band showed 98% identity to the 3'-untranslated region within exon 19 of 10.2 kb human MAP-2 cDNA (GenBank Accession No. U32996; nucleotides 1931–2384). It has been shown that cDNA probes derived from this region detect 6- and 9 kb alternative splice variants of MAP-2 mRNAs which produce, respectively, the juvenile 70 kDa MAP-2 and an ~280 kDa mature MAP-2a and b (Gamer C C., et al., *J. Cell Biol.,* 106:779–783 (1988)).

A 410-bp PCR amplified cDNA fragment nested within the 450-bp differential display fragment was amplified by PCR using a set of primers flanking the region of MAP-2 cDNA identical to the DD-PCR fragment, and used to probe Northern blots of polyA-enriched RNA isolated from control and HMBA treated metastatic melanoma (SK-MEL-19 and SK-MEL-23 c22) cells. The oligonucleotides used to generate the MAP-2 probe were the sense oligonucleotide MAP-2cF: (SEQ ID NO: 2: 5'-ATCAAATGGTCCACTAGGCG-3'), and the antisense oligonucleotide MAP-2cR (SEQ ID NO: 3:5'-GCACTTCAAGGGAAGCTGAT-3').

Northern analysis was performed as described (Fang, D., et al., *Biochem. Biophys. Res. Commun.,* 256:657–63 (1999)) using the Northern Max kit and Strip-EZ DNA probe synthesis and removal kit (Ambion, Inc., Austin, Tex.). In control (untreated) SK-MEL-19 and SK-MEL-23 cl.22 metastatic melanoma cells, a weak 6 kb band representing the alternatively spliced MAP-2 mRNA could be seen (FIG. 4A). In SK-MEL-19 cells treated with HMBA for 48 h, a 4-fold increase in MAP-2 mRNA was noted. Prolonged presence of the inducer resulted in continued accumulation (up to 12-fold) of MAP-2 in SK-MEL-19 cells (FIG. 4B). Thus, Northern analysis confirmed the identification of MAP-2 as a differentially expressed gene in melanoma cells treated with the differentiation inducer HMBA.

Blots were also probed with a probe for TYRP1, generated as described by Fang et al., (*Biochem. Biophys. Res. Commun.,* 256:657–63 (1999)). It can be seen that along with an increase in MAP-2, there is a concomitant down-regulation of the melanocyte differentiation marker TYRP1 by HMBA in SK-MEL-19 and SK-MEL-23 cl.22 cells (FIG. 4A, middle panel). The relative intensities for each probe were obtained by normalizing to GAPDH.

Example 5

Expression of MAP-2 in Melanoma Cell Lines

Figure 5:
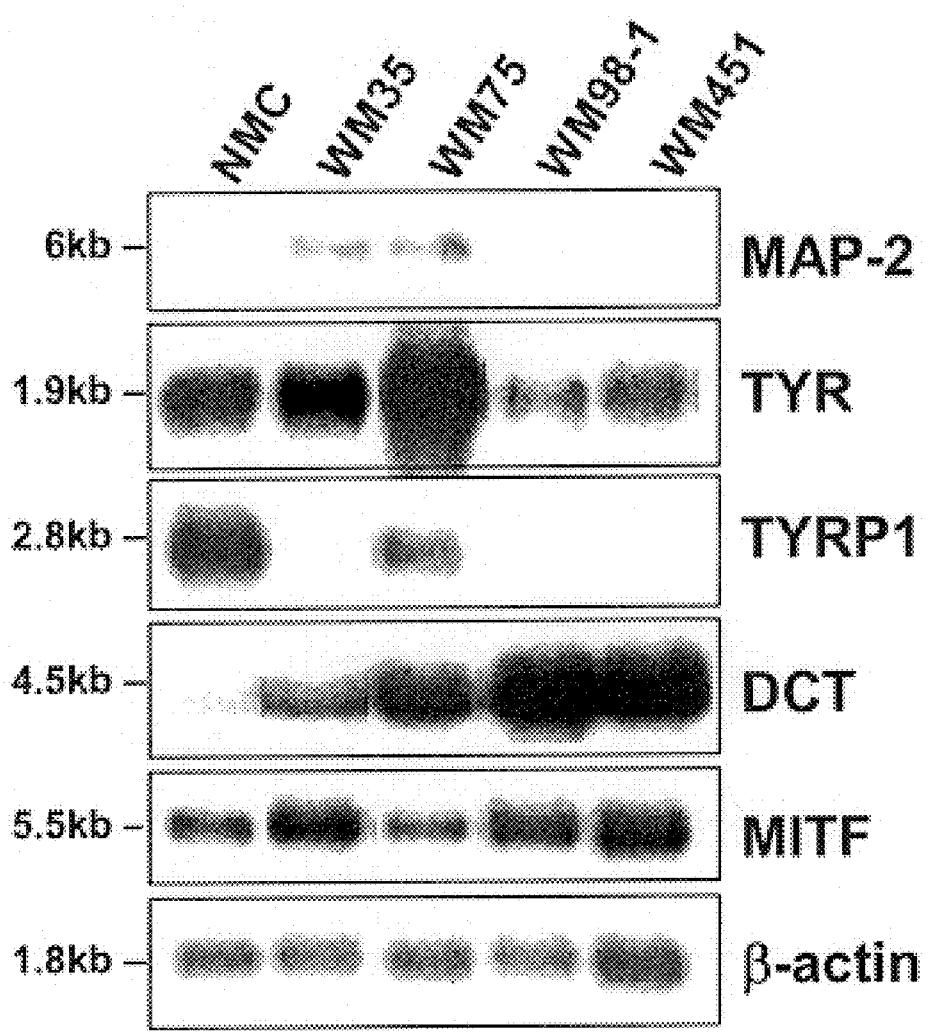
FIG. 5 shows an aspect of an embodiment of the invention comprising expression of MAP-2 mRNA and other markers TYR (tyrosinase), TYRP1, tyrosinase-related protein-2 (i.e. dopachrome tautomerase, DCT) microphthalmia-associated transcription factor (MITF), and β-actin, in human melanocytes and melanoma as measured by Northern blot analysis of 3 μg poly A$^+$ RNA isolated from cultured neonatal melanocytes (NMC), primary RGP melanoma cell line WM35, primary VGP melanoma cell lines WM75 and WM98-1, and metastatic melanoma cell line WM451.

Expression of MAP-2 was studied in a panel of well-characterized cell lines that represent melanoma progression. PolyA-enriched RNA isolated from neonatal foreskin melanocytes, primary melanoma cell lines WM35 (radial growth phase), WM75 and WM98-1 (vertical growth phase), and metastatic melanoma WM45 1, was analyzed by Northern blot hybridization (FIG. 5). In primary melanoma cell lines WM3 5 and WM75, the 6 kb MAP-2 mRNA representing the juvenile transcript was readily detected. MAP-2 mRNA was not detected, however, in normal melanocytes, primary melanoma WM 98-1, or metastatic melanoma WM451.

The variable expression of melanocyte differentiation markers tyrosinase, TYRP1, DCT and MITF in these cell lines is also shown in FIG. 5. Thus, melanocytes in the early stage of tumor progression activate transcription of the early neuronal differentiation markers MAP-2 and produce an alternatively processed MAP-2c transcript normally found in immature neurons.

Example 6

Expression of MAP-2 Protein

Western blot analysis was used to detect the expression of MAP-2 protein. Western blot analysis was performed as described by Fang, D., et al., (*Biochem. Biophys. Res. Commun.,* 256:657–63 (1999)). Cells were solubilized in lysis buffer containing 1% SDS, 10 mM Tris pH 7.4 and proteinase inhibitors (Boehringer Mannheim, Indianapolis, Ind.). Samples comprising approximately thirty micrograms of protein, as estimated using the BCA protein assay (Pierce, Rockford, Ill.), were subjected to 9% sodium dodecyl sulfate polyacrylamide gel electrophoresis (SDS-PAGE), and transferred electrophoretically to a PVDF membrane (NEN Life Science, Boston, Mass.). Blots were incubated in TBS blocking buffer (1% BSA in 10 mM Tris pH 7.5; 100 mM NaCl) at room temperature for 3 h, and then at 4° C. overnight with primary antibodies diluted in TBS (10 mM Tris pH 7.5; 100 mM NaCl). Antibodies used were anti-MAP-2 monoclonal antibodies (mAbs), HM-2 (Sigma), and M13 antibody (Zymed Laboratories, San Francisco, Calif.) diluted 1:1000, and anti-γ-tubulin polyclonal antibody (Sigma) diluted 1:5000. Membranes were washed several times with TBST (TBS containing 0.1% Tween 20), and blots were incubated 1–3 hours with either horseradish peroxidase labeled donkey anti-mouse (for HM-2 and M13 antibodies) or horseradish peroxidase labeled anti-rabbit antibody (for γ-tubulin antibody) (Amersham Pharmacia Biotech Inc., Piscataway, N.J.) diluted 1:2000–1:2500 in TBST. After washing with TBST, protein bands were detected by chemiluminescence using an ECL kit (Amersham Pharmacia Biotech Inc.).

First, the specificity of available anti-MAP-2 antibodies was tested. As shown in FIG. 6A, HM-2 mAb detected both the immature juvenile ~70 kDa and mature ~280 kDa isoforms of MAP-2 found in 1-day old rat brain extracts, and the 280 kDa mature form in the adult brain extracts. M13 mAb, on the other hand, detected only the mature ~280 kDa form in newborn and adult rat brain extracts. Western blot analysis of detergent extracts of melanoma cell lines with mAB HM-2 is shown in FIG. 6B. The ~70 kDa band corresponding to the MAP-2c isoform could be detected in WM35, WM75 and all primary melanoma cell lines tested and the metastatic cell line SK-MEL-19, but not in normal melanocytes. In SK-MEL-19 cells treated with HMBA, an increase in the amount of MAP-2c protein was apparent. Although the 9 kb mRNA that produces the mature ~280 kDa protein was not detectable by Northern blotting, a faint protein band corresponding to the MAP-2a, -2b isoforms could be detected in these melanoma cell lines. For comparison, amounts of these isoforms detectable in newborn rat brain extracts are also shown (end lane in FIG. 6B), although the rat brain isoform appears to migrate slightly slower than the ~70 kd doublet of the rat brain isoform.

Example 7

MAP-2 Expression in Vivo

Immunohistochemical detection of MAP-2 expressed in human melanocytic lesions was performed to characterize expression of MAP-2 in vivo. Tissue specimens were fixed in 10% neutral buffered formalin (10% in phosphate buffer), and embedded in paraffin using methods standard in the art. Standard sections were cut on positively charged slides and immunohistochemical studies for TYRP1 (mel-5; Signet Laboratories; Dedham, Mass.; diluted 1:80) and gp100 (HMB45) (Dako Corporation; Carpinteria, Calif.; diluted 1:100), Melan A/MART-1 (Novocastra Laboratories; Burlingame, Calif.; 1:5), neuron-specific enolase (NSE; Dako; Glostrup, Denmark; 1:50), neurofilament protein p68 (Accurate Chemical and Scientific Co.; Westbury, N.Y.; 1:5), low affinity nerve growth factor receptor (p75NGFR; Boehringer Mannheim; Indianapolis, Ind.; 1:40), and neural adhesion molecule (CD56/N-CAM; Becton-Dickinson; San Jose, Calif.; 1:40) were performed using immunoperoxidase staining with a Ventana autostainer (Ventana Medical Systems; Tucson, Ariz.). Immunohistochemical studies for MAP-2 (M-13; Zymed; pre-diluted) were performed manually using the manufacturer's Histontain-Plus Kit, which employs a standard streptavidin-biotin amplification method and a 3-amino-9-ethylcarbazole (AEC) chromogen.

A total of 61 individual paraffin-embedded lesions were incubated with mAb M13 for detection of the mature variant of MAP-2. The samples used included 10 congenital and acquired melanocytic nevi, 9 primary malignant melanomas, and 42 metastatic melanomas. Whereas the majority of nevi (60%) and many primary melanomas (44%) were strongly MAP-2 positive (+++ to ++), only a small percentage of metastatic melanomas (24%) had foci of MAP-2 stained cells (Table I). Fisher's exact test showed a strong association between the number of lesions showing strong MAP-2 reactivity and the characteristics of the melanocytic lesions (P=0.0039). As shown in FIG. 7A, in a malignant melanoma arising in a nevus, both the dermal nevus cells, and the cells within the early primary melanoma showed strong cytoplasmic staining for MAP-2. TYRP1 specific mAb MEL-5 stained melanocytes and melanoma cells within epidermis and at the dermal-epidermal junction, while the early invasive disease and the intradermal nevus cells were less intensely stained.

In cutaneous primary melanomas showing in situ and more extensive invasive components, a majority of the invasive component was strongly positive for MAP-2 (FIG. 7B; lower panels show higher magnification). Metastatic lesions excised from the left arm and brain from the same patient showed negative or weakly positive staining, respectively, for MAP-2 (not shown). Conversely, TYRP1 expression was restricted mostly to the in situ and junctional component. Cells within the tumor nests either showed weak expression or were TYRP1 negative.

A limited number of primary superficial spreading malignant melanomas and associated nevi were also studied for expression of additional neuronal markers, specifically neuron-specific enolase (NSE), neurofilament protein p68, neural adhesion molecule (CD56/N-CAM), and low affinity nerve growth factor receptor (p75NGFR). Significant expression of NSE was found in both nevus and melanoma components. Whereas no expression of neurofilament protein p68 or CD56/N-CAM could be detected in either component, p75NGFR expression was found to be restricted to malignant melanocytes in situ. All primary melanomas tested showed expression of melanocytic markers gp100 and MelanA/MART-1 (data not shown).

In the small percentage of metastatic melanomas that were positive for MAP-2, the immunoreactivity was heterogeneous with a few cells and/or small clusters showing intense cytoplasmic staining, while adjacent cells were devoid of MAP-2 expression (FIG. 7C). Tumor cells within metastatic lesions, including those stained positive with mAb HMB45, were negative for TYRP1 expression (FIG. 7C).

TABLE I

Immunohistochemical staining of melanocytic lesions with anti-MAP-2 antibody

| | | MAP-2 Staining Intensity | | | |
|---|---|---|---|---|---|
| Lesion | N | +++ | ++ | + | − |
| Nevi | 10 | 6 (60%) | 0 (0%) | 1 (10%) | 3 (30%) |
| Primary Melanoma | 9 | 3 (33.3%) | 1 (11.1%) | 2 (22.2%) | 3 (33.3%) |
| Metastatic Melanoma | 42 | 2 (5%) | 8 (19%) | 14 (33%) | 18 (43%) |

In Table I, the relative intensity of staining of paraffin embedded tissue section with mAb M13 is shown as (−): no detectable immunoreactivity, or (+), (++) and (+++):

increasing intensity of reactivity, where N=number of specimens tested. Data are shown as the number of specimens positive or negative for MAP-2 staining (numbers in parenthesis are percent total specimens). Nevi include both congential and acquired types; primary melanomas include 2 desmoplastic specimens and 7 conventional melanomas, and metastatic melanomas include 26 lesions from lymph nodes, 13 from brains and 3 other anatomical sites (one lesion each from lung, bone and parotid gland). Analysis of the data using Fisher's exact test (r×c contingency table) showed strong association between intensity of MAP-2 staining and the characteristics of the melanocytic lesions studied (P=0.0039).

Example 8

Regulation of MAP-2 Expression

The effects of phorbol ester TPA (a modifier of protein kinase C) and cholera toxin (a cAMP inducer) on MAP-2 expression in melanoma cells are shown in FIG. 8. SK-MEL-19 cells were treated with the phorbol ester 12-O-tetradecanoyl phrobol-13-acetate (TPA) or cholera toxin (CT) for 6, 24 and 48 hours (h) and MAP-2 expression measured by Northern blot analysis of total RNA. As shown in FIG. 8, treatment of cells with TPA or CT did not induce MAP-2 expression, although up-regulation of MAP-2 expression was detected in cells treated with HMBA by 48 h. When HMBA was added together with TPA or CT, however, significant increases in MAP-2c mRNA could be detected as early as 6 h after treatment.

Similarly, whereas treatment with TPA or cholera toxin alone did not cause down-regulation of TYRP1 mRNA, treatment with HMBA alone or in combination with TPA or cholera toxin resulted in extinction of TYRP1 expression (FIG. 8). These data suggest that while agents that activate protein kinase C and cAMP pathways do not directly increase MAP-2 expression in melanoma, they can facilitate MAP-2 induction by other agents such as HMBA, and the like. Furthermore, there is a reciprocal relationship between pathways that regulate the expression of the melanocytic marker TRP-1 and the neuronal marker MAP-2 in melanoma cells.

With respect to the descriptions set forth above, optimum relationships, to include variations in specific components and manner of use, are deemed readily apparent and obvious to those skilled in the art, and all equivalent relationships to those illustrated in the drawings and described in the specification are intended to be encompassed herein. The foregoing is considered as illustrative only of the principal of the invention. Since numerous modifications and changes will readily occur to those skilled in the art, it is not intended to limit the invention to the exact embodiments shown and described, and all suitable modifications and equivalents falling within the scope of the appended claims are deemed within the present inventive concept.

It is to be further understood that the phraseology and terminology employed herein are for the purpose of description and are not to be regarded as limiting. Those skilled in the art will appreciate that the conception on which this disclosure is based may readily be used as a basis for designing the structures, methods and systems for carrying out the several purposes of the present invention. The claims are regarded as including such equivalent constructions so long as they do not depart from the spirit and scope of the present invention.

What is claimed is:

1. A method for detecting MAP-2 protein in a sample comprising tumor cells comprising the steps of:
    (a) obtaining a test sample comprising tumor cells, wherein said tumor cells comprise melanoma cells;
    (b) incubating said cells with an antibody that forms a complex with MAP-2 protein or fragments thereof; and
    (c) determining the presence of the complex.

2. The method of claim 1, further comprising comparing the levels of MAP-2 protein in said sample relative to at least one control comprising known amounts of MAP-2.

3. The method of claim 2, further comprising assessing the risk of whether the tumor sample comprises increased metastatic potential based on the level of MAP-2 in the tumor relative to the control.

4. The method of claim 1 further comprising:
    (a) obtaining a control sample comprising non-metastatic melanoma cells;
    (b) determining whether MAP-2 protein or fragments thereof are present in the control sample; and
    (c) comparing the amount of MAP-2 in the test sample relative to the control sample; wherein the presence of decreased levels of MAP-2 protein in the test sample relative to the level of MAP-2 in non-metastatic control cells indicates that the test sample has increased metastatic potential as compared to the control.

5. The method of claim 4, wherein said test sample comprises invasive melanoma.

6. The method of claim 4, wherein said test sample is from a patient.

7. The method of claim 6, wherein reduced MAP-2 protein in the test sample as compared to a non-metastatic control indicates the test subject is at risk of developing metastatic disease.

8. A method for determining the metastatic potential of a tumor sample comprising the steps of:
   (a) obtaining a test tumor sample of unknown metastatic potential from a subject;
   (b) determining the level of MAP-2 expression in said test sample; and
   (c) assessing the metastatic potential of the sample based on the level of MAP-2 expression in the test sample relative to a non-metastatic control.

9. The method of claim 8, wherein the presence of decreased levels of MAP-2 expression in the test sample relative to the level of MAP-2 expression in non-metastatic controls indicates that the sample has increased metastatic potential as compared to the control.

10. The method of claim 8, wherein the levels of MAP-2 expression is assessed in comparison to controls comprising known amounts of MAP-2.

11. The method of claim 8, wherein the level of MAP-2 expression in said cells from said sample and said control is assessed by measuring the level of MAP-2 protein, or fragments thereof, in said cells.

12. The method of claim 11, further comprising:
    (a) disrupting the cellular membrane of said cells to allow access to intracellular proteins;
    (b) incubating said cell proteins with a detection agent which recognizes and complexes with MAP-2 protein or fragments thereof; and
    (c) detecting the presence of said complex.

13. The method of claim 12, wherein said detection agent comprises antibody which recognizes MAP-2 protein or a fragment thereof.

14. The method of claim 8, wherein the sample comprises tumor cells.

15. The method of claim 8, wherein the sample comprises tumor cells derived from the neural crest.

16. The method of claim 8, wherein the sample comprises melanoma cells.

17. The method of claim 8, wherein the sample comprises invasive melanoma.

18. The method of claim 8, wherein said test sample is from a test subject.

19. The method of claim 18, wherein reduced MAP-2 expression in the test sample as compared to a non-metastatic control indicates that the test subject is at risk of developing metastatic disease.

* * * * *

UNITED STATES PATENT AND TRADEMARK OFFICE
CERTIFICATE OF CORRECTION

PATENT NO.    : 6,613,534 B2
DATED         : September 2, 2003
INVENTOR(S)   : Vijayasaradhi Setaluri, Dong Fang and Wain White It is certified that error appears in the above-identified patent and that said Letters Patent is hereby corrected as shown below:

Column 1,
Line 13, that portion reading "Kobayash, N. et al.," should read -- Kobayashi, N. et al., --
Line 18, that portion reading "and metastatic melanomas," should read -- "and metastatic malignant melanomas," --
Line 33, that portion reading "enhances translation of mRNA late after infection," should read -- enhances translation of mRNAs later after infection, --

Column 2,
Line 7, that portion reading "Without Increasing Cyclic-AMP, Metab. Res. 31:402-5" should read -- Without Increasing Cyclic-AMP, Horm. Metab, Res. 31:402-5" --
Line 24, that portoin reading "Sangueza, O. et al., Neoplasmas with Neural Differentiation:" should read -- "Sangueza, O. et al., Neoplasms with Neural Differentiation: --

Column 11,
Line 1, that portion reading "0.05% sodium pyrophosphate at 37° C. for a 14 base" should read -- 0.05% sodium pyrophosphate at 37° C for a 14 base --
Lines 3 and 4, that portion reading "or at 55° C. for a 20 base oligonucleotide, or at 60° C. for a 25 base oligonucleotide, or at 65° C. for a nucleotide probe" should read -- or at 55° C for a 20 base oligonucleotide, or at 60° C for a 25 base oligonucleotide, or at 65° C for a nucleotide probe --
Lines 8 and 9, that portion reading "sodium dodocyl sulfate (SDS), 1mM EDTA At 65° C., and washing in 0.1xSSC/0.1% SDS at 68° C. (see e.g. Ausubel," should read -- "sodium dodocyl sulfate (SDS), 1mM EDTA at 65° C , and washing in 0.1×SSC/0.1% SDS at $68^0$ C (see e.g. Ausubel," --

Column 17,
Line 28, that portion reading "Rilfind, R.A.," should read -- Rifkind, R.A., --
Line 30, that portion reading "protein kinase Ce" should read -- protein kinase C∈ --

UNITED STATES PATENT AND TRADEMARK OFFICE
CERTIFICATE OF CORRECTION

PATENT NO. : 6,613,534 B2
DATED : September 2, 2003
INVENTOR(S) : Vijayasaradhi Setaluri, Dong Fang and Wain White It is certified that error appears in the above-identified patent and that said Letters Patent is hereby corrected as shown below:

Column 19,
Line 59, that portion reading "at 4° C. overnight." should read -- at 4°C overnight. --

Column 20,
Line 65, that portion reading "55-60° C. for 20 min with 0.5%xSSC" should read -- 55-60°C for 20 min with 0.5%xSSC --

Column 23,
Line 3, that portion reading "NaCl) at room temperature for 3 h, and then at 4° C." should read -- NaCl) at room temperature for 3 h, and then at 4°C --

Signed and Sealed this

Fourteenth Day of September, 2004

JON W. DUDAS
*Director of the United States Patent and Trademark Office*